(12) United States Patent
Parish et al.

(10) Patent No.: US 7,973,658 B2
(45) Date of Patent: Jul. 5, 2011

(54) ILLUMINATION AND DETECTION ARCHITECTURE

(76) Inventors: Warren G. Parish, Sarasota, FL (US); Tim Arion, Melbourne, FL (US)

( * ) Notice: Subject to any disclaimer, the term of this patent is extended or adjusted under 35 U.S.C. 154(b) by 0 days.

(21) Appl. No.: 12/722,513

(22) Filed: Mar. 11, 2010

(65) Prior Publication Data

US 2010/0164718 A1    Jul. 1, 2010

Related U.S. Application Data

(63) Continuation of application No. 11/352,800, filed on Feb. 13, 2006, now Pat. No. 7,750,802.

(60) Provisional application No. 60/652,151, filed on Feb. 11, 2005.

(51) Int. Cl.
*G08B 21/00* (2006.01)

(52) U.S. Cl. ..... 340/540; 340/541; 340/550; 340/545.5; 340/539.17; 340/539.2; 250/390.04; 250/370.01; 356/71; 356/72; 356/73; 356/301; 356/318; 356/320; 356/436; 356/437

(58) Field of Classification Search ............... 340/540, 340/541, 550, 545.6, 539.17, 539.2; 250/390.04, 250/370.01; 356/71, 72, 73, 301, 318, 320, 356/436, 437

See application file for complete search history.

(56) References Cited

U.S. PATENT DOCUMENTS

| | | | |
|---|---|---|---|
| 5,141,312 A | 8/1992 | Thompson et al. | |
| 5,438,360 A | 8/1995 | Edwards | |
| 5,443,793 A | 8/1995 | Ehrlich et al. | |
| 5,652,651 A | 7/1997 | Dunne | |
| 5,760,898 A | 6/1998 | Haley et al. | |
| 6,201,493 B1 | 3/2001 | Silverman | |
| 6,773,674 B2 | 8/2004 | Bannister et al. | |
| 6,984,524 B2 | 1/2006 | Nguyen et al. | |
| 7,088,435 B2 | 8/2006 | Brestel et al. | |
| 7,180,418 B1 | 2/2007 | Willms et al. | |
| 7,298,475 B2 * | 11/2007 | Gandhi et al. | 356/318 |
| 2004/0008345 A1 | 1/2004 | Nurmikko et al. | |
| 2004/0220753 A1 | 11/2004 | Tabe | |
| 2005/0156734 A1 | 7/2005 | Zerwekh et al. | |
| 2006/0023211 A1 | 2/2006 | Gandhi et al. | |
| 2006/0249683 A1 | 11/2006 | Goldberg et al. | |

* cited by examiner

*Primary Examiner* — Tai T Nguyen
(74) *Attorney, Agent, or Firm* — Eric D. Jorgenson, Esq.

(57) ABSTRACT

An illumination and detection architecture that illuminates a target for detecting a material of interest. The architecture includes an illumination component that illuminates the target using a predetermined light wavelength known to energize and thereby cause a detectable change in the desired chemical and/or compounds associated with the target in a particular way. The change is then captured by an image capture system and processed to determine the presence or absence detected of the desired material of interest at the target.

20 Claims, 21 Drawing Sheets

ILLUMINATION AND DETECTION ARCHITECTURE

CROSS-REFERENCE TO RELATED APPLICATIONS

This application is a Continuation of U.S. patent application Ser. No. 11/352,800 entitled "ILLUMINATION AND DETECTION ARCHITECTURE" and filed Feb. 13, 2006, now U.S. Pat No. 7,750,802, which claims the benefit of U.S. Provisional Patent Application Ser. No. 60/652,151 entitled "TARGET COMPOSITION DETECTION ARCHITECTURE" and filed Feb. 11, 2005. The entireties of the above-noted applications are incorporated by reference herein.

TECHNICAL FIELD

This invention is related to illumination and detection systems for detecting the presence or absence of materials of a target object using image capture and processing techniques.

BACKGROUND

The security of any country is becoming threatened more and more by individuals who seek to impose their own beliefs on the society by destabilizing the current governments, taking retribution against others, and/or to profit illegally from sales of drugs and guns, for example. Accordingly, governments are devoting more resources to combat such efforts. Airports and borders are being more closely monitored for individuals and the transport of illegal materials trying to enter (or leave) a country.

The detection and monitoring of trace amounts of explosives and/or drugs, for example, can be a daunting task; however, this is critical to providing a safe environment for the population. Current methods include x-ray detection and other nuclear techniques for non-human examination, such as at airports for luggage, none of which address the possibility that such materials can be carried by the person. Similarly, such applications are not conducive to use in a field or war setting where explosives are oftentimes carried on the person (e.g., soldiers and machinery) or buried out of sight (e.g., land mines and booby traps). Accordingly, a need exists for improved techniques, systems, and methodologies for detecting materials of interest.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The subject innovation facilitates detection of materials on and/or proximate a target. In order to do so, energy is imposed on the target and/or target area from an energy source such that desired materials of the target on which the energy is imposed cause a detectable change to occur that indicates the presence of the desired material(s). The type of energy as well as characteristics and/or parameters of the energy are controlled to trigger presence or absence of the selected material at the target. For example, where the imposed energy is light, the frequency can be controlled to cause optically detectable changes at the target.

The invention disclosed and claimed herein, in one aspect thereof, comprises an illumination and detection system that facilitates detection of a target material. The system includes an illumination component for directing photon energy of a predetermined wavelength at a target, which target is associated with a material of interest, and which photon energy causes a detectable change to occur in the material of interest at or near the target. A detection component is providing for detecting the change by imaging the change data and facilitating notification of the detected change to a user.

In another aspect of the subject invention, the architecture illuminates and detects that the chemical characteristics of the target vapor plume includes an explosive and/or a drug.

In another aspect, the architecture illuminates and detects that a change associated with particulates of a material of interest that can be on a surface and/or absorbed into the surface of the target.

In yet another aspect thereof, the illuminator and detector architecture is employed an integral handheld system that is portable so that a single user can carry and operate the handheld system to apply illumination and detect the target chemical properties.

In still another aspect thereof, the illumination is provided from an overhead vehicle such as an airplane and/or a helicopter, and the detector system is land-based. In another implementation, the illumination system is land based.

In another aspect, the illuminator includes a laser, and the detector subsystem includes is night-vision scope tuned to detect the change in the target. The illuminator and detector systems can also be assembled and operated as separate portable systems or as a single portable system.

To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
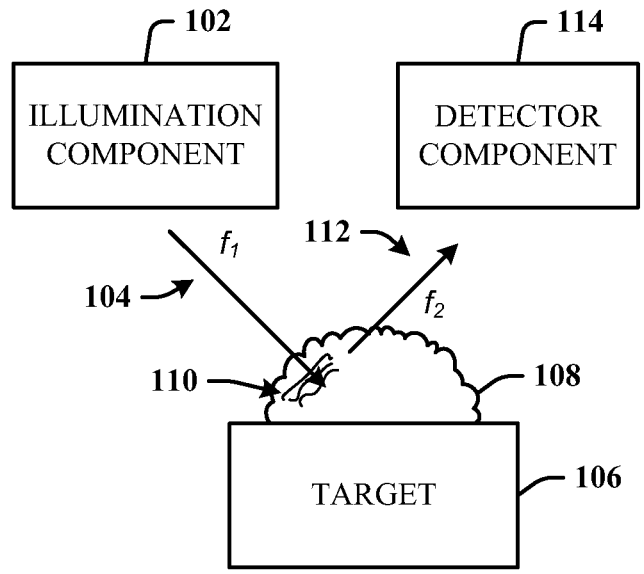
FIG. 1 illustrates a system that facilitates the illumination and detection of one or more materials of a target via an associated vapor plume in accordance with the subject invention.

The invention is now described with reference to the drawings, wherein like reference numerals are used to refer to like elements throughout. In the following description, for purposes of explanation, numerous specific details are set forth in order to provide a thorough understanding of the subject invention. It may be evident, however, that the invention can be practiced without these specific details. In other instances, well-known structures and devices are shown in block diagram form in order to facilitate describing the invention.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

The subject innovation facilitates detection of materials on and/or proximate a target. In order to do so, energy is imposed on the target and/or target area from an energy source such that desired material(s) of the target on which the energy is imposed exhibit a detectable change that can be processed to determine the presence or absence of the desired material(s). It is to be understood that the term "change" as used herein is intended to include any one or more of detectable events such as a chemical change, photoluminescent events such as fluorescence and phosphorescence, photofragmentation or photodisassociation, to name a few. The type of energy as well as characteristics and/or parameters of the energy are controlled to facilitate detecting the presence or absence of the selected material at the target. For example, where the imposed energy is light, the frequency can be controlled to cause detectable changes in vapors at the target and/or particulates on the surface or slightly beneath the surface of the object.

Referring initially to the drawings, FIG. 1 illustrates a system 100 that facilitates the illumination and detection of one or more materials of a target via an associated vapor plume (or material outgassing) in accordance with the subject invention. The system 100 can include an illumination component 102 that provides a source of electromagnetic radiation 104 (also referred to herein as "illumination" or "light") that can be directed onto a target 106. The radiation 104 can be of a frequency that is visible or not visible to the human eye. For example, the illumination component 102 can be a LASER (Light Amplification of Stimulated Emission of Radiation—hereinafter, "laser"), which facilitates directing a visible coherent source of light onto the target 106. In another implementation or in combination with other light sources, light-emitting diodes (LED's) can be employed.

The target 106 can include the material of interest desired to be detected. For example, if the target 106 includes an explosive, it would be desirable under many difference circumstances to know not only that there is an explosive, but what type of explosive.

The chemical composition of many types of materials, whether natural or manmade, is such that the objects including such materials typically, or coming into contact with such materials, can in many cases, continually or periodically, emit (or outgas) one or more gasses or vapors associated with the materials. Thus, there is an invisible atmospheric vapor plume or cloud 108 that exists in some volume of space proximate the target 106 and that can include chemical vapors associated with one or more types of materials of interest in, on, and/or around the target 106. In the example of FIG. 1, the vapor cloud 108 is shown to one side of the target 106, where the target 106 is a 3-D object, as opposed to the target 106 being an area or surface; however, it is to be understood that in 3-D space, the vapor cloud 108 can be on some or all sides of the target 106.

In operation, the illumination component 102 imposes the light 104 at a predetermined frequency $f_1$ (or frequency range $f_1$-$f_r$) on the target 106, and when doing so, impacts the vapors 108. The energy of the light 104 interacts with a certain chemical or chemicals in the vapor plume causing a detectable change 110. For example, the change can be detectable at a different frequency $f_2$ (or frequency range $f_1$-$f_d$) of detectable light 112 by a detector component 114 that can include one or more image sensors and associated processing capability suitable for imaging and processing of the image data. Given that it would be known beforehand that the image data of the detected change would be associated with a certain material (or compound, e.g., an explosive) when energized by the light at the frequency $f_1$, it would be readily determinable that the material of interest is present or absent at the target 106.

The change 110 occurs and is detectable only as long as the light (or energy) 104 is imposed on the vapors 108 of the target 106 (or area) at the desired frequency (or wavelength). Thus, once the light 104 is removed from the target 106, the vapor change 110 can be undetectable by the detector component 114.

Figure 2:
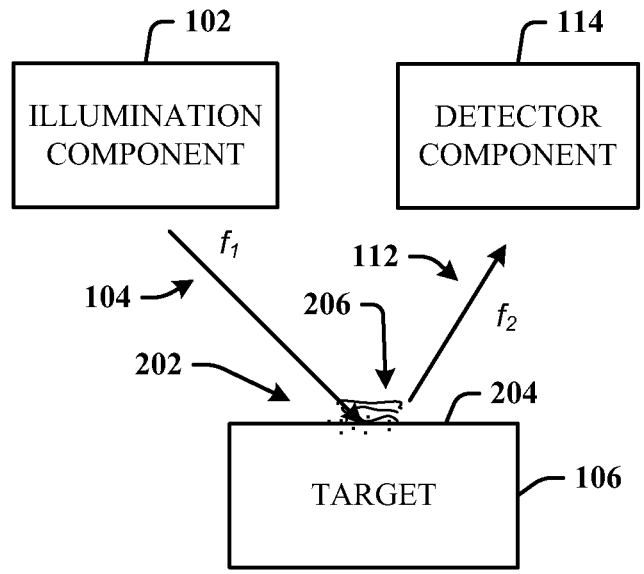
FIG. 2 illustrates a system that facilitates the illumination and detection of one or more materials of a target via associated particulates on or beneath a surface of the target, in accordance with an innovative aspect.

FIG. 2 illustrates a system 200 that facilitates the illumination and detection of one or more materials of a target via associated particulates 202 on a surface 204 and/or absorbed into the target 106, in accordance with an innovative aspect. It is to be appreciated that the target 106 to be examined could also have come into contact with the particulates 202 of the material of interest such as associated with dust, particulates in oil, a liquid, and/or minute particles on the surface 204 or have been absorbed or migrated beneath the surface.

The system 200 can include the same illumination component 102 that provides a source of electromagnetic radiation 104 that can be directed onto the target 106, and of a frequency that is visible or not visible to the human eye, such as a laser. The target 106 can include the particulate material of interest (e.g., explosive, drug, . . . ) desired to be detected. For example, if the target 106 includes a drug, it would be desirable under many difference circumstances to know not only that there is a drug, but what type of drug.

Where a surface of the target 106 has been exposed or contacted by the material of interest, residual particulates 202 of dust and/or smear of liquid, oil, etc., can exist on the surface which includes chemicals which when illuminated at the desired wavelength, exhibit a change that can be detected. In one example, the surface 204 can be the surface of the earth (also referred to herein as "ground") such that if the particles 202 associated with the material of interest, for example, drifted to the ground, again, illumination on those particles 202 could be detected in accordance with the imaging and analysis techniques of the system 200.

In operation, the illumination component 102 imposes the light 104 at a predetermined frequency $f_1$ (or frequency range $f_1$-$f_r$) on the target 106, and when doing so, impacts the particles 202. The energy of the light 104 interacts with a certain chemical or chemicals of the particles causing a change 206 that is detectable at a different frequency $f_2$ (or frequency range $f_1$-$f_d$) of detectable light 112 by the detector component 114 that includes one or more image sensors and associated processing capability suitable for detecting the desired material of interest energized by the illumination component 102. The change 206 occurs and is detectable only as long as the light (or energy) 104 is imposed on the particles 202 of the target 106 (or area) at the desired frequency (or wavelength). Thus, once the light 104 is removed from the target 106, the change 206 reverts back to its original state, and hence, is no longer detectable by the detector component 114.

The systems (100 and 200) are particularly suited for detecting drugs and/or explosives of near and/or distant locations. For example, in one implementation, trace amounts of nitrocompounds and other energetic materials in the atmosphere or on surfaces can be detected, for example, compounds related to DMNA (N,N-dimethylnitrosamine), nitromethane, nitrobenzene, TNT, and RDX (Cyclotrimethylenetrinitramine) or RDX compositions, to name just a few.

The source component 102 can also be configured to work using a fluorescent light source and/or an incandescent light sources (e.g., 50/60 Hz), for example, using special coatings that facilitate providing the desired frequency, and insofar as the light imposed causes a detectable change in the vapor 108 and/or particles associated with the material of interest to be detected at the target 106.

Accordingly, excitation of a molecule, for example, of the material of interest can be detected under a phenomenon called photoluminescence, which includes two categories of fluorescence and phosphorescence. Fluorescence is the property of some atoms and molecules to absorb light at a particular wavelength and to emit light at longer wavelengths after a brief interval known as a fluorescence lifetime. The process of phosphorescence occurs in a similar manner, but with a much longer lifetime of the excited state.

It is also to be appreciated that the illumination component 102 and the detector component 114 can be interconnected such that the components (102 and 114) are controlled by a central control system. In another implementation, the components (102 and 114) are housed in a common chassis that is portable. In yet another implementation, the components (102 and 114) are integrated into a handheld portable chassis for use by a single user. These implementations are described in greater detail infra.

Figure 3:
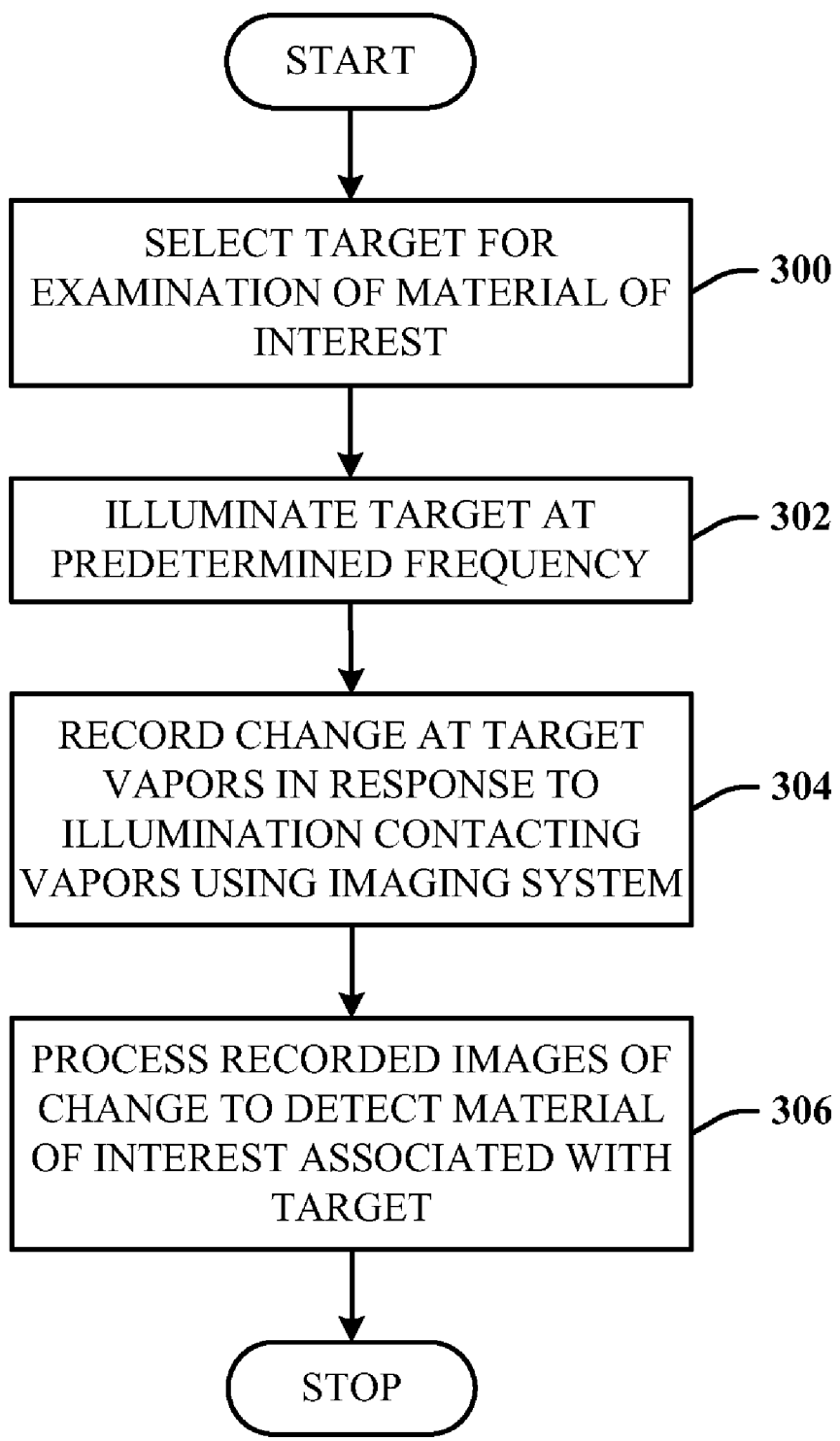
FIG. 3 illustrates a methodology of target illumination and material detection for target vapors in accordance with the invention.

FIG. 3 illustrates a methodology of target illumination and material detection for target vapors in accordance with the invention. While, for purposes of simplicity of explanation, the one or more methodologies shown herein, for example, in the form of a flow chart, are shown and described as a series of acts, it is to be understood and appreciated that the subject invention is not limited by the order of acts, as some acts may, in accordance with the invention, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the invention.

At 300, a target object and/or area is selected for examination for the material of interest. Selection can be simply by a user visually selecting the target and then illuminating the target such that the vapors proximate thereto exhibit a detectable change as caused by the light of a predetermined frequency. Another implementation includes illuminating the target area in which the desired target chemical(s) (or material of interest) is expected to be. In this case, if the target chemical is in this area, it will be detected according to the illumination and detection capabilities described herein. At 302, given the particular chemical compound or trait that is desired to be detected, light from the source is adjusted to a predetermined wavelength (or frequency(ies)) and directed at the target. At 304, the system detects and records a change at the vapors proximate to the target using an imaging system. As described herein, chemical vapors exist in an acquiescent (or ambient) state when the energizing light at the predetermined wavelength is not illuminating (or imposed on) the vapors, and the vapors are in a changed (or energized) state when the light illuminates the vapors at the predetermined wavelength. At 306, the changed state information, as captured in the images, is received from the imaging system and, analyzed and processed to determine if the change is associated with the material of interest.

It can be possible that the captured change information indicates a false positive. Under such circumstance, it is beneficial to run the analysis and processing over several samples (or images) in order to arrive at results that have a high likelihood of being correct, whether it represents that the material of interest is present or not.

Figure 4:
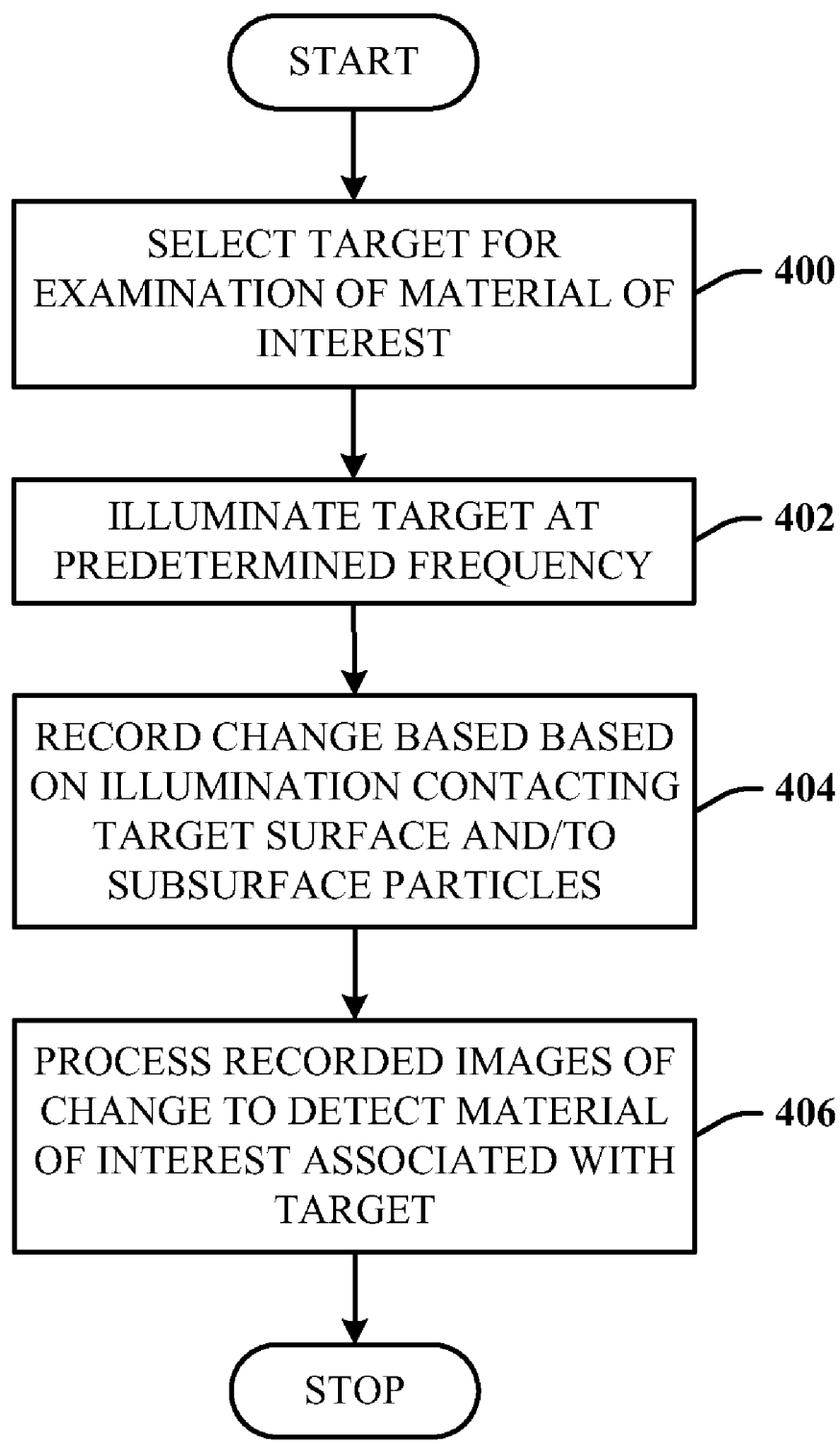
FIG. 4 illustrates a methodology of target illumination and material detection for target particulates in accordance with the invention.

FIG. 4 illustrates a methodology of target illumination and material detection for target particulates in accordance with the invention. At 400, a target object and/or area is selected for examination for the material of interest. Selection can be simply by a user visually selecting the target and then illuminating the target such that the particles proximate thereto exhibit a detectable change as caused by the light of a predetermined frequency. Another implementation includes illuminating the target area in which the desired target chemical(s) (or material of interest) is expected to be. In this case, if the target chemical is in this area, it will be detected according to the illumination and detection capabilities described herein. At 402, given the particular chemical compound or trait that is desired to be detected, light from the source is adjusted to a predetermined wavelength (or frequency(ies)) and directed at the target. At 404, the system detects and records a change at the particles proximate to the target or on the target using an imaging system. At 406, the changed state information, as captured in the images, is received from the imaging system, analyzed and processed to determine if the change is associated with the material of interest.

Figure 5:
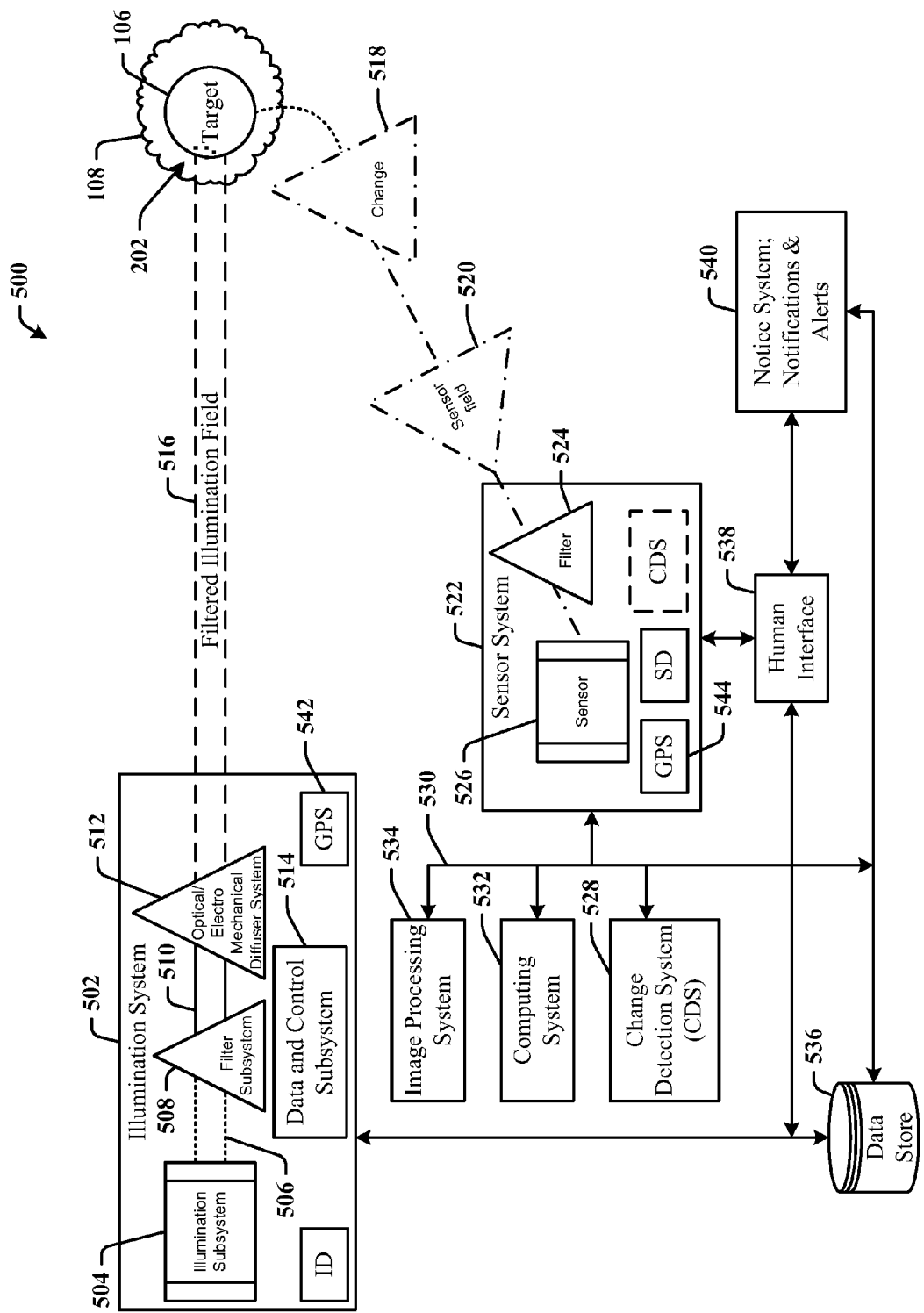
FIG. 5 illustrates a block diagram of a system for illumination and detection in accordance with an innovative aspect.

Referring now to FIG. 5, there is a diagrammatic illustration of a system 500 for illumination and detection in accordance with an innovative aspect. An illumination system 502 provides illumination of the target 106. The illumination system 502 includes an illumination source subsystem 504 (e.g., a laser) that outputs light 506 (visible or not), which light 506 is then filtered through a filter subsystem 508. The filter subsystem 508 can be used to achieve a predetermined wavelength by filtering out unwanted wavelengths that may provide "false positives". The output of the filter subsystem 508 is a filtered light 510 which can be then diffused using an optical/electromechanical diffuser subsystem 512. The diffuser subsystem 512 facilitates tactical diffusing of the filtered light beam 510. It is to be appreciated that the diagram of the illumination system 502 is simplistic, in that typically, other optical elements and components can be employed to facilitate providing the desired output. In this particular implementation, the illumination system 502 can further include a data and control subsystem 514 that allows for powering the components of the system 502, controlling any of the system components (e.g., the illumination subsystem 504, the filter subsystem 508, and/or diffuser subsystem 512), acquiring and storing data related thereto, and related to the target 106, and communications components for communicating information of the system 502.

The output of the diffuser subsystem 512 is a filtered illumination field 516 that is directed to impact the vapors 108 and/or particles 202 of the target 106. Once impacted, the vapors 108 and/or particles 202 proximate the target 106 exhibit a change, as denoted at 518, which change 518 is within a sensor field 520 of a sensor system 522. The sensor system 522 can include at least a filter 524 and a sensor 526 suitable for facilitating capture of the change 518 exhibited by the target vapors 108 and/or particles 202. The sensor 526 captures certain photons associated with the change using the sensor filter 524 that limits the incoming target light to a certain frequency or frequencies. The output of the sensor subsystem 522 can be processed for display by a computing system or to an eyepiece for viewing by a human, or both. It is to be appreciated that a human does not need to perceive the detected data or its representation in any way. This means that the data can be processed automatically to trigger further processes such as alerts and notifications, for example.

At this point, the system 500 provides the capability of illuminating the target 106 in order to detect a predetermined type of target material using a predetermined illumination wavelength that will cause a change which can be captured by the sensor system 522. Such sensor data can be of greater use through analysis and processing for determining the chemical composition of the target 106. The invention is most advantageously applied in dangerous environments where there is a great risk to human life, such as in law enforcement and the military, in determining the presence of chemicals normally associated with drugs, poisonous materials (e.g., powders, and gases), explosives, and/or explosive compounds.

In support thereof, the system 500 further includes a change detection system (CDS) 528, which in this implementation is external to the sensor system 522, such that raw sensor data is passed externally from the sensor system 522 over a conventional wired or wireless communications pathway 530 for further analysis and processing; however, it need not be external. That is, the change detection system 528 can be optionally implemented internal to the sensor system 522 (indicated by a dashed-line block denoted CDS) such that an output of the sensor system 522 is simply the change information detected.

When processed externally, a computing system 532 can be employed on the pathway 530 to facilitate data processing and analysis. The sensor system 522 can also communicate over the pathway 530 with an image processing system 534 that facilitates the capture, analysis, and processing of the change data detected at the target 106. Thus, a person can view the detected change data (e.g., from vapor and/or particulates) in any way desired, via the image processing system 534 and/or the computing system 532. Note that it is to be appreciated that the capabilities of the image processing system 534 can be combined into the computing system 532 and with the change detection system 528. The change detection subsystem 528 can be employed to receive images from the image processing system 534, and process those images to detect the change. As indicated, however, these blocks can be combined into a single entity that performs both functions.

Any data generated, received, and/or detected by the system 500 can be stored in a data store 536, and in any data format desired, as would be associated with conventional data models (e.g., a relational database and an object oriented database). The data store 536 can interface to the illumination system 502 and the sensor system 522 to provide data thereto (e.g., the illumination system 502) and receive data for storage and later access (e.g., the sensor system 522). It is to be further appreciated that the data store 536 can be non-volatile chip memory (e.g., flash memory) suitable for rugged outdoor and industrial environments. The data store 536 can be implemented in combination with separate data stores which are employed separately in the illumination system 502 and the sensor system 522, indicated respectively as an illumination data store (ID) and a sensor data store (SD).

The system 500 can also include a human interface component 538 that interfaces to the sensor system 522, the data store 536, the illumination system 502, and a notice system (e.g., communications and alerts) 540. In another implementation, the interface component 538 can further interface to any or all of the CDS 528, computing system 532 and/or the video processing system 534.

In addition to analyzing and processing the detected change information, the results can be used to further trigger other processes. For example, if the detected change 518 indicates that the target 106 is explosives, a warning and/or message/instructions can be automatically transmitted using the notice system 540. The notice system 540 can interface both to the human interface 538 and the data store 536, such that the alert can be initiated by a human and/or automatically initiated based on data stored, accessed and processed by the notice system 540 from the data store 536. The notice system 540 can facilitate presentation of alerts and/or notifications to the human user via the human interface 538 by way of textual and/or graphical visual indicators (e.g., via a graphical user interface), audio indicators, and/or electromechanical means (e.g., a vibratory signal, electrical signal, . . . ), for example.

Other capabilities such as conventional geographical location systems can be employed. For example, a GPS (Global Positioning System) subsystem 542 can be included in the system 500 (e.g., the illumination system 502) to provide geolocation data (e.g., latitude/longitude coordinates) for the location of the system 500. Alternatively, or additionally, the sensor system 522 can include a GPS subsystem 544 that can be employed to accurately locate it.

Still further, either or both of the GPS subsystems (542 or/and 544) can be used to define the approximate location of the target 106, for other purposes. The GPS information obtained from one or both of the GPS subsystems (542 or/and 544) can also be processed and stored. As indicated herein, the GPS data can also be used to determine the approximate range to the target 106.

Other geolocation techniques can be employed alternatively or additionally to GPS. For example, triangulation can be employed between two location devices. Where the illumination system 502 and the sensor system 522 are separate systems and sufficiently oriented to facilitate triangulation, the approximate location of the target 106 can be determined relative to either of the systems (502 or 522). In yet another implementation, signal strengths of wireless communications can be analyzed and processed to determine the geolocation of the system 500 and/or subsystems (502 and 522).

A rudimentary implementation of the subject innovation can be via a handheld pen laser tuned to the desired frequency and employed in combination with a night-vision scope configured to sense the vapor change of the desired chemical(s).

Figure 6:
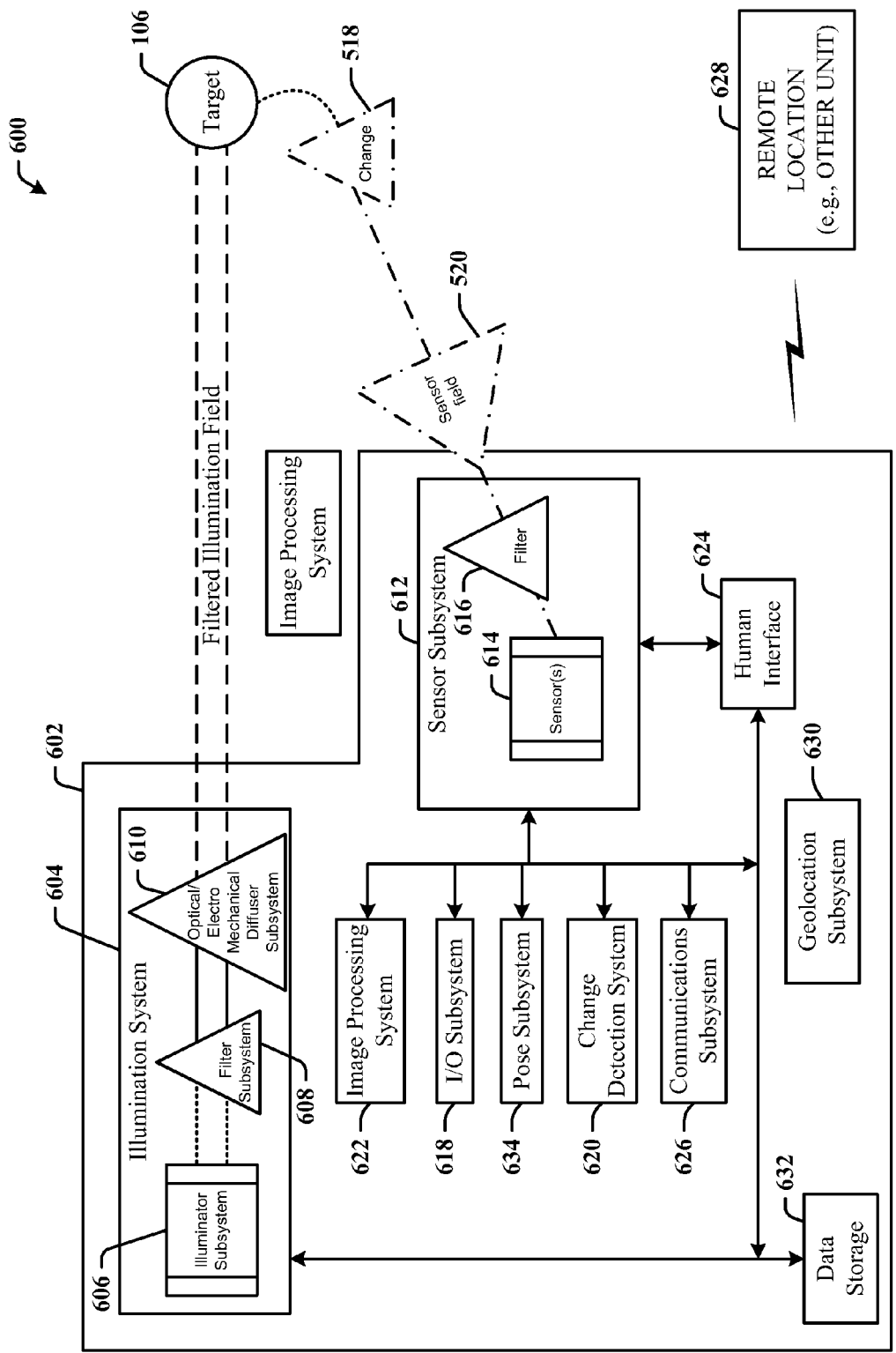
FIG. 6 illustrates a block diagram of an alternative illumination and detection system in accordance with an aspect.

FIG. 6 is a diagrammatic illustration of an alternative illumination and detection system 600 in accordance with an aspect. Here, the system 600 embodies components into an integral unit 602, which can be a portable unit and/or a handheld unit. The unit 602 includes an illumination subsystem 604 which comprises an illuminator subsystem 606, a filter subsystem 608, and an optical/electromechanical diffuser subsystem 610. The unit 602 further includes a sensor subsystem 612 that includes at least one sensor 614 for sensing a change and a filter 616 for filtering the change information 518 from the sensor field 520 for processing.

It is to be appreciated that the unit 602 can employ a presentation (or display) system such that a user can not only impose illumination on the target 106 (e.g., in a general area in which the detectable material of interest is anticipated to be), but also view the resulting change information and/or associated indication in accordance with a representation that the user chooses. In support thereof, the unit 602 can further include an I/O (Input/Output) subsystem 618 that facilitates I/O transfer between the sensor subsystem 612 and other internal components of the unit 602. For example, the unit 602 can also include a change detection system 620 that facilitates detection of the change associated with the material of interest at the target 106, an image processing system 622 that facilitates displaying to a user via a human interface system 624 data representative of the detected change, and a communications subsystem 626 that facilitates wired and/or wireless communications with a remote location and/or another unit 628.

A geolocation subsystem 630 (e.g., GPS) can utilize the communications subsystem 626 for receiving and/or transmitting geolocation signals for determining an approximate geolocation of the unit 602 and/or the target 106. The unit 602 can also include a data storage subsystem 632 for the storing and access of data and/or applications employed for controlling the internal subsystem of the unit 602. The human interface component 624 allows a user to interact with the unit 602 for the use and control thereof.

The system 600 can also include a pose subsystem 634 for estimating location and orientation of the unit 602 within its environment. Pose estimation techniques include pose from hardware and pose from video. Hardware pose estimation can be obtained via GPS and/or inertial navigation systems, for example. Video pose estimation uses camera images that estimate pose of the system or unit by calculating interframe camera motion from image features. It is to be understood that the pose subsystem 634 can be employed, optionally. Additionally, the pose subsystem can be employed separately in either or both of the illumination system 502 or/and the sensor system 522 of FIG. 5, for example.

Figure 7:
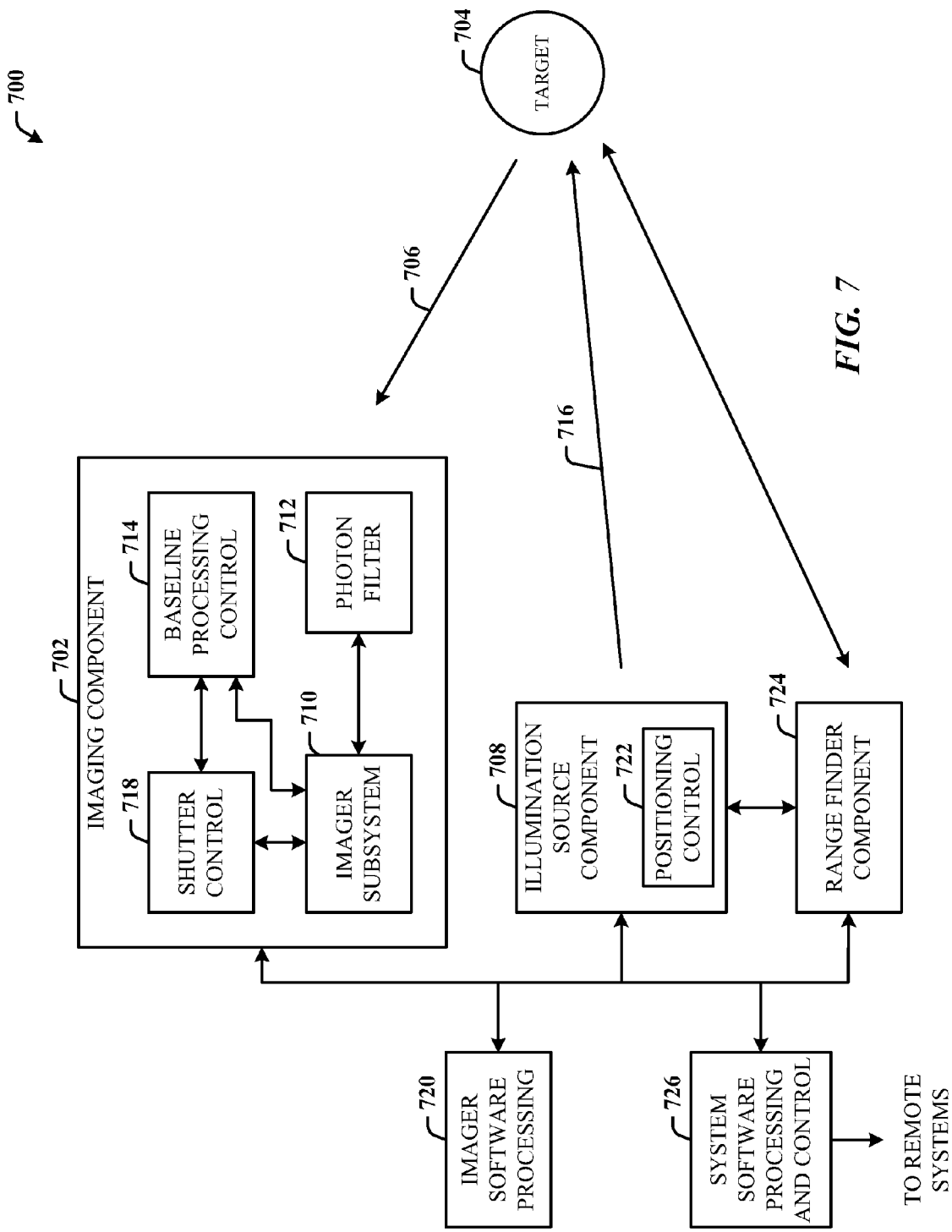
FIG. 7 illustrates a block diagram of a system that includes an imaging component for image detection and processing of a detectable change at a target.

FIG. 7 illustrates a block diagram of a system 700 that includes an imaging component 702 for image detection and processing of a detectable change at a target 704. The imaging component 702 receives target information 706 related to a detectable change at the target 704 as a result of being illuminated by an illumination source component 708.

The imaging component 702 can include subsystems that facilitate initialization (and/or self calibration) and baseline processing for eliminating effects of ambient conditions, for example. In support thereof, the component 702 can include an imager subsystem 710 for receiving the target information 706 as photons that are filtered through a photon filter 712 to remove unwanted signals. The component 702 can also include a baseline processing control component 714 that facilitates initialization and/or calibration of the imager subsystem 710 prior to capturing a reading of the target information 706. For example, it is desired to eliminate the effects of the ambient lighting conditions by first capturing the ambient or background lighting data for eventual subtraction or elimination from the final image data. Next, capture of the working conditions can be recorded by briefly imposing illumination 716 on the target 704 with the illumination component 708, and then capturing an image so as to process the illuminated target data against the ambient lighting conditions to obtain a delta value.

The imaging component 702 can also include a shutter (or baffle) control component 718 that closes off substantially all light to the imager elements to allow any residual readings (or photon activity) on the active elements of the imager to subside or bleed off. It is to be appreciated that such shutter can be opened and closed in short periods of time (e.g., milliseconds) in support of making the initialization process very short in terms of time. This will be controlled to reach the desired "black" criteria or residual photon activity on the imager before initiating the next image capture.

Once the ambient lighting conditions, affects of illumination on the target, and residual imager conditions have been measured and accounted for, detection of the desired material of interest at the target can commence. Accordingly, when the illumination 716 is imposed on the target 704, the imager subsystem 710 receives back photon information from the target 704 related to the ambient lighting conditions and the light on target impact, which are then processed and subtracted out. What remains should be any change information recorded in the snapshot or image as captured by the imager 710. It is to be appreciated that this process can be performed many times in a very short period of time, thereby receiving large amounts of data which can be processed to confirm or deny or provide a likelihood of the presence or absence of the material of interest. Such processing can be provided by an imager software processing component 720. This processing component 720 can include high speed processing hardware (e.g., digital signal processors) and/or software for the rapid analysis, processing, and turnaround of imaging data in order to obtain results.

The illumination source component 708 can also include a positioning control component 722 (e.g., a servo control device) for controlling the direction of illumination to the target 704. Accordingly, the illumination 716 (e.g., a beam from a laser) can be finely controlled to impact the target 704.

The system 700 can also, optionally, include a range finder component 724 for determining an approximate distance-to-target value. This distance value can be used to control the illumination on the target 704. For example, if the distance value exceeds a predetermined minimum distance value, it will be understood that some adjustment to the illumination beam 716 may be required, for example, related to focus or dispersion thereof. On the other hand, if the distance value is less than the minimum value, the beam 716 may not require further adjustment prior to examining the target for the material of interest. Range determination can be accomplished by several different techniques, such as laser detection and/or high frequency sonic means, for example.

The system 700 can also include a system software processing and control component 726 for process and control of any of the aforementioned components. In particular, if the range finder component 724 returns a value which indicates that the illumination component 708 requires adjustment, the process and control component 726 can interface to the positioning control component 722 to achieve the desired adjustment in the illumination beam 716, with respect to at least the amount of dispersion and placing the beam on the target 704.

Figure 8:
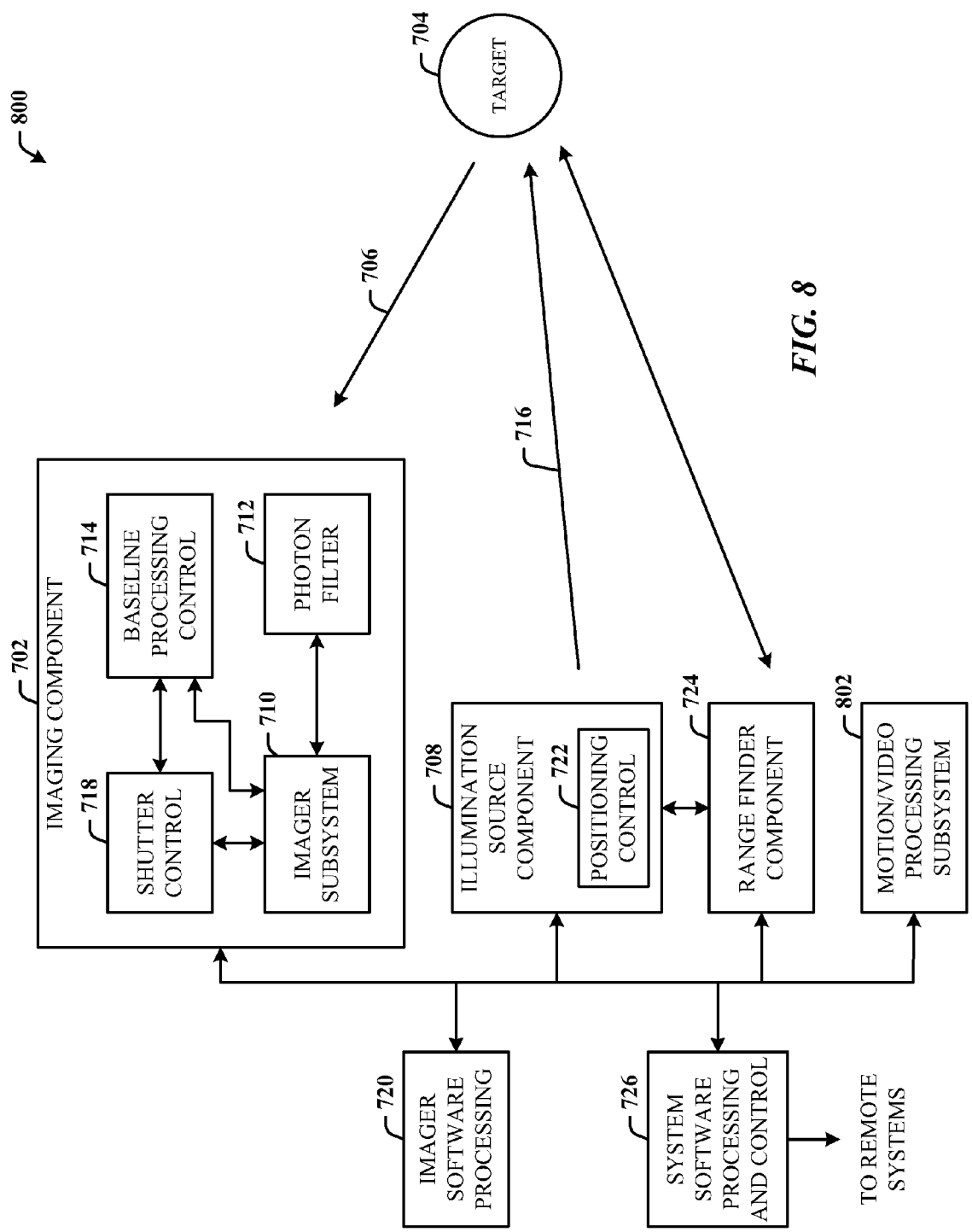
FIG. 8 illustrates the block diagram of a system similar to the system of FIG. 7 but further employing a motion processing subsystem in accordance with an innovative aspect.

FIG. 8 illustrates the block diagram of a system 800 similar to the system 700 of FIG. 7 but further employing a motion processing subsystem 802 in accordance with an innovative aspect. The subsystem 802 is employed as a means of compensating for motion imposed on one or more of the system 800 components. For example, if the illumination source 802 was deployed on a vehicle moving down a road, the road surface, being uneven, can cause the point of imposition of illumination beam 716 on the target 704 to vary, and perhaps, even miss the target 704. The motion processing subsystem 802 can process motion data and seek to compensate for motion imposed on the illumination component 708, for example.

In one implementation, the imaging component 702 can be employed to not only capture change information at the target 704, but also to detect and compensate for motion of the illumination component 708 relative to the target 704. For example, the imager can be operated to take snapshots of the target 704 as predetermined intervals (e.g., thirty frames per second, faster or slower), and the data of each frame (or image) can be compared to previous frames to determine the direction of motion at that time. Dynamically, the imager software processing component 720 can pass data to the positioning control component 722 that is processed to servo control the illumination source(s) to maintain the illumination 716 on target 704.

In another implementation, employed separately or in combination with the imaging motion compensation function, the motion subsystem 802 can employ accelerometers to measure triaxial (x, y, and z coordinates) directional measurements which indicate the vector of motion having a direction and magnitude which can be utilized for input to the positioning control component 722 to maintain servo control of a servo motor that controls position or orientation of the illumination source.

It is to be understood that where the illumination source component 708 includes multiples light sources, that each of the sources can be servo controlled independently to maintain its beam on the target 704.

The other components of FIG. 8, previously described in FIG. 7, can operate and function as described supra. For example, the imaging component 702 for calibration, initialization, image detection and processing of a detectable change at the target 704, the imager software processing component 720 for high speed processing hardware and/or software for the rapid analysis, processing, and turnaround of imaging data, the illumination component 708 for illuminating the target 704, the positioning control component 722 for controlling the direction of illumination to the target 704, the range finder component 724 for determining an approximate distance-to-target value, and the system software processing, and the processing and control component 726 for additional process and control capability of any of the aforementioned components.

It is to be understood that may different types of data can be transmitted to remote locations for further processing and analysis. Here, such data output is shown from the processing and control component 726; however, such data can be received from some or all of the other components, as desired.

It is further to be appreciated that the system 800 can dispense with the range finder subsystem 724 while retaining the motion processing subsystem 802. Moreover, the illumination component 708 can be deployed separately from the imaging component 702.

Figure 9:
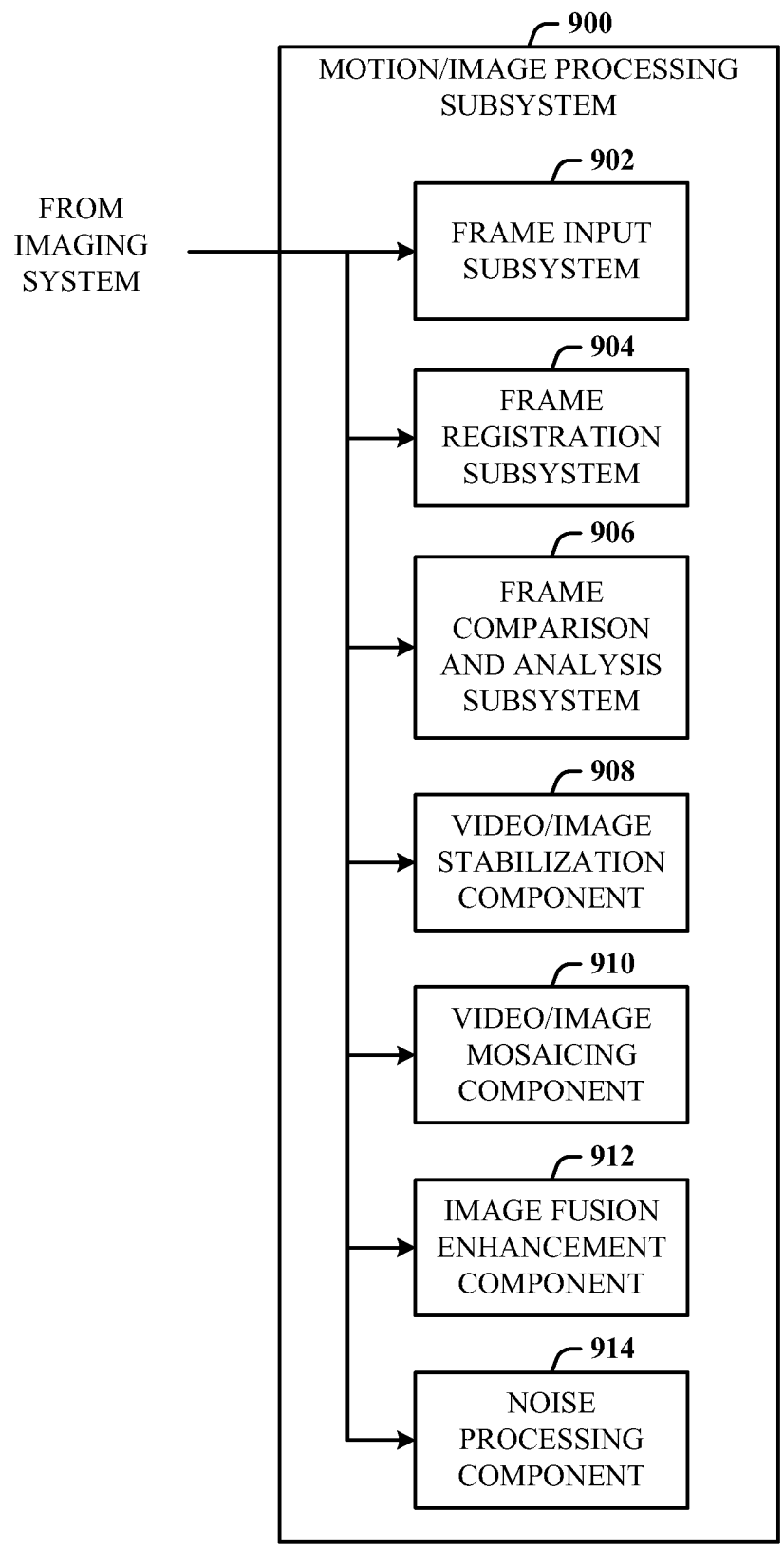
FIG. 9 illustrates a more detailed block diagram of a motion processing subsystem, similar to the motion processing subsystem of FIG. 8.

FIG. 9 illustrates a more detailed block diagram of a motion/video processing subsystem 900, similar to the motion subsystem 802 of FIG. 8. Here, the subsystem 900 can further include a frame input subsystem 902 that receives frame (or image snapshot) information from the imaging component 702 of FIG. 8. The input subsystem 902 can process the input frames to provide at least one or more of storage, caching, normalization and/or formatting functions prior to further analysis and processing. When a sufficient number of frames have been received and processed at the frame input subsystem 902, frame registration can occur via a frame registration subsystem 904. This can include alignment (or registration) of one frame with another frame to insure a proper frame registration. After registration, frame analysis and comparison can commence via a frame comparison and analysis subsystem 906. This process can include estimating direction and magnitude of the motion so as to properly control the illuminator(s) for placing the beam on target. As illustrated, data output from this subsystem 900 can be motion compensation data that is fed to the positioning control component 722 of FIG. 8.

The system 900 can also employ a video (or image) stabilization component 908 for management of the impact of camera vibration on the resulting images. This can include image processing technology (hardware and/or) to reduce camera shake that has a greater impact on the images when the camera zooms to a distant object. One technique that can be employed selects an image detail from which to differentiate between background images and shake input to the image. Such vibratory signals can be introduced from noisy video sources, large object movement nearby or in the scene, and operation of mechanical functions associated with zoom, tilt, and pan, for example.

The system 900 can also include a video/imaging mosaicing component 910 for video enrichment. Mosaicing is commonly used for increasing the visual field by "pasting" together many video frames or images creating a single image and generating a panoramic view. As the camera moves across a view, projection parameters can be obtained by reconstructing camera movements made during the filming. Translational movements can also be made of the camera or imager. Conventional techniques that can be employed to compensate for forward motion and zoom include manifold projection. As well, view interpolation can be employed for generating dense intermediate views and parallax effects, as one example.

Video mosaicing also provides for temporal and spatial interpretability. In other words, it facilitates faster access to critical video events, and enables moving object detection. Additionally, mosaicing provides significant compression capabilities (on the order of 100:1), is lossless, and can be extended to standard compression techniques. In one implementation, the difference in information from one frame to the next (or the delta) is iteratively appended to the previous frame to ultimately arrive at the panoramic view. Only the delta information need be stored.

The system 900 can also include an image fusion component 912 for context enhancement when combining images that have been captured under different illumination. The component can also facilitate extending the dynamic range and depth of focus of an imaging sensor through pattern selective color image fusion, for example.

A noise processing component 914 can also be employed to suppress noise. Such noise suppression techniques can be system based on one or both of spatial and temporal information. Temporal information can be realized through a sequence of images that contain exactly the same objects, but only differ in independent noise introduce into each frame. Where the noise is additive simple averaging can be employed to reduce the noise. Where temporal averaging is not possible, other techniques can be employed to decrease the noise, such as, for example, spatial averaging (e.g., via smoothing algorithms such as median filtering, Gaussian filtering Kuwahara filtering and morphological smoothing).

Although not shown here, but as are known to one skilled in the art, the system 900 can utilize other image processing subsystems/components to improve and/or address the desired image processing needs. Moreover, it is to be understood that not all of the components shown in the system 900 are required.

Figure 10:
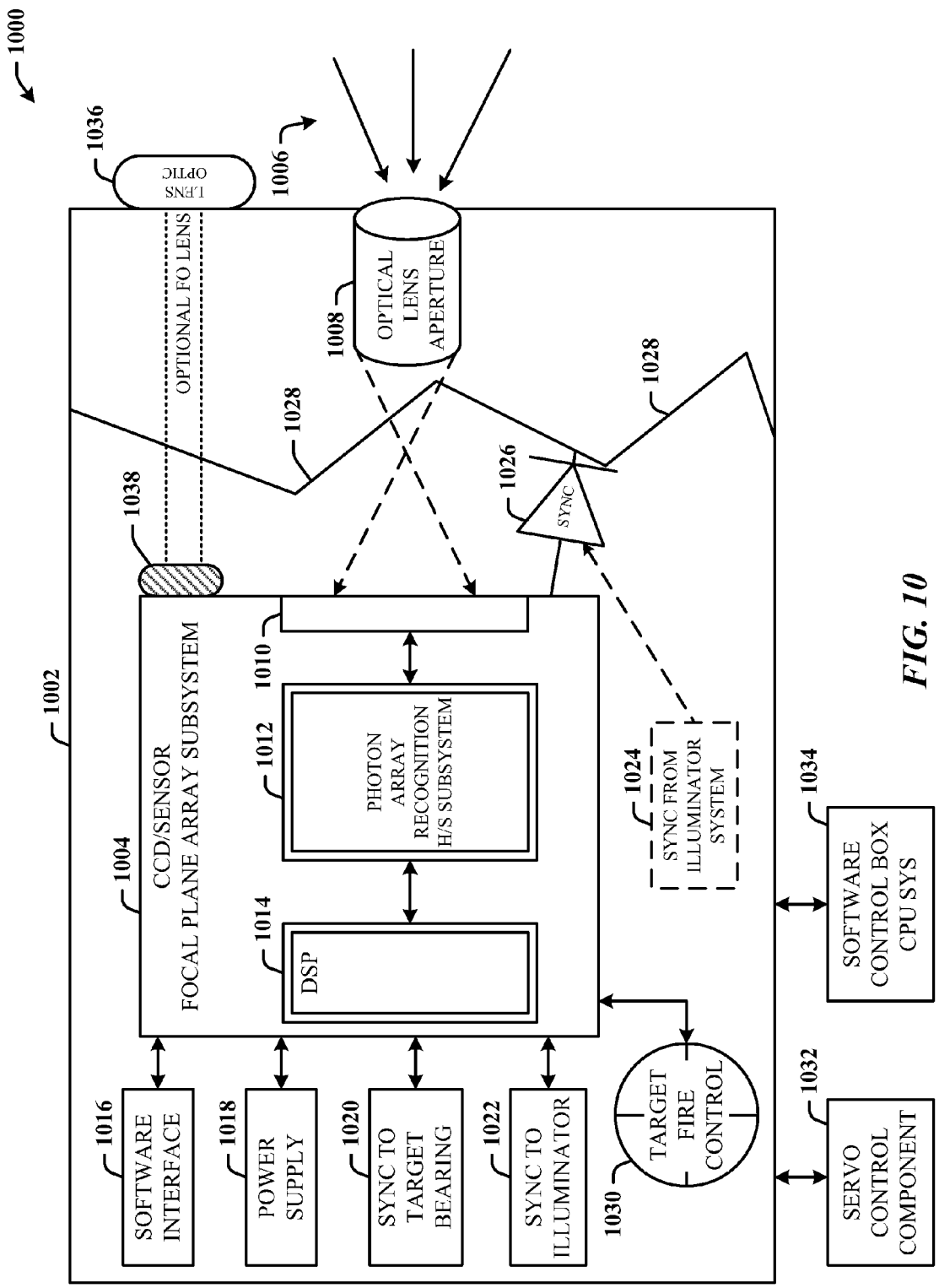
FIG. 10 illustrates an exemplary imaging system in accordance with an innovative aspect.

FIG. 10 illustrates an exemplary imaging system 1000 in accordance with an innovative aspect. The system 1000 can include a sensor housing 1002 in which most of the subsystems are constructed. In the housing 1002 can be an imager (e.g., CCD-charge coupled device) sensor subsystem 1004 (e.g., focal plane array (FPA) such as infrared FPAs, near IRFPAs, . . . ) for sensing photons 1006 associated with a change at the target. Other types of imagers can also be employed. The photons 1006 can be received through an optical lens aperture apparatus 1008 which facilitates directing the received photons to an imager 1010 of the sensor subsystem 1004. The sensor subsystem 1004 can further include a photon array recognition hardware/software subsystem 1012 that receives data representative of the photon signatures captured on elements of the imager 1010, which data can then be processed by a high speed processor (e.g., a DSP) 1014.

Other subcomponents in the housing 1002 of the system 1000 can include a software interface component 1016 for providing an interface to other systems. A power supply 1018 provides power to all necessary system entities. A first synchronization subcomponent 1020 facilitates synchronization of imager data with a bearing of the target. A second synchronization subcomponent 1022 facilitates synchronization of imager data to an illuminator (not shown). That is, it is desired that illumination only be applied to the target when needed. Since illumination will be applied via another subsystem, synchronization with when the target is illuminated and when the imaging system should be set for receiving detected information needs to be coordinated. Synchronization signals from the illuminator can also be received and processed via block 1024 to drive a sync control subsystem 1026 for baffle control of a baffle (also referred to herein as a shutter) subsystem 1028. Data from the sensing subsystem 1004 can also be communicated between the sensing subsystem 1004 and external fire control systems via a target fire control interface subsystem 1030.

A servo control component 1032 interfaces to the housing 1002 for automatic and/or dynamic orientation of the housing 1002 for fast and reliable capture of the change detected at the target. Additionally, an external software control component 1034 can provide processing capabilities for the system 1000.

The sensor subsystem 1004 can also interface to an optional fiber optic (FO) lens 1036 that can facilitate receiving optical signals into the sensing subsystem 1004, which can connect to the sensing subsystem 1004 via optical glue 1038.

Figure 11:
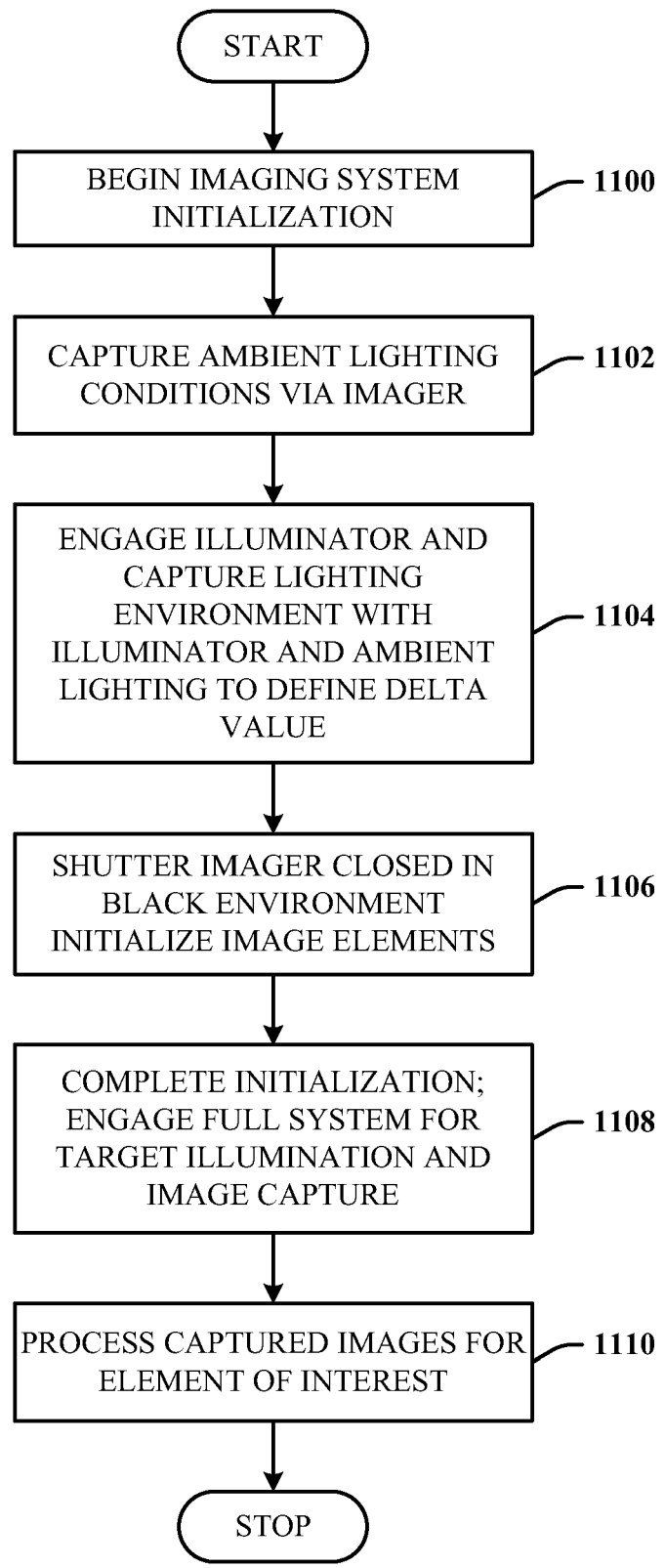
FIG. 11 illustrates a methodology of calibrating and initializing an imaging subsystem in accordance with the invention.

FIG. 11 illustrates a methodology of calibrating and initializing an imager subsystem in accordance with the invention. At 1100, imaging system initialization is commenced. It is to be appreciated that such an operation can be conducted after each illumination of the target, after a predetermined time that the target has been illuminated, or when in pulse mode, after a series of illumination pulses have been imposed on the target. A benefit of pulse mode illumination is that if the target has been overly energized, the impact of such over-energization can affect the target material of interest thereby tainting the result, and perhaps resulting in a false positive. For example, a high energy laser can "burn off" substances its beam impacts at the target. Thus, by pulsing the beam on and off, the duration of exposure of the target material to the energizing beam can be controlled so as to not cause this to happen. Similarly, such high energy application can cause micro-explosions on gases and/or particles impacted by the beam, again, tainting the results.

At 1102, the imaging system captures ambient lighting conditions for processing. At 1104, the target is briefly illuminated to determine the effects to the illumination on the target, and for computing a delta value for the difference in lighting between the ambient or background photonic "noise" and the light received from illumination of the target. At 1106, the shutter or baffle is activated to place the imager in black mode to obtain a "black" measurement for the active elements before performing the actual target examination process. At 1108, when initialization has completed, the full system can be engaged for target examination and image capture. At 1110, the images received from target examination are processed for detecting the change information which indicates the presence of the material of interest.

Figure 12:
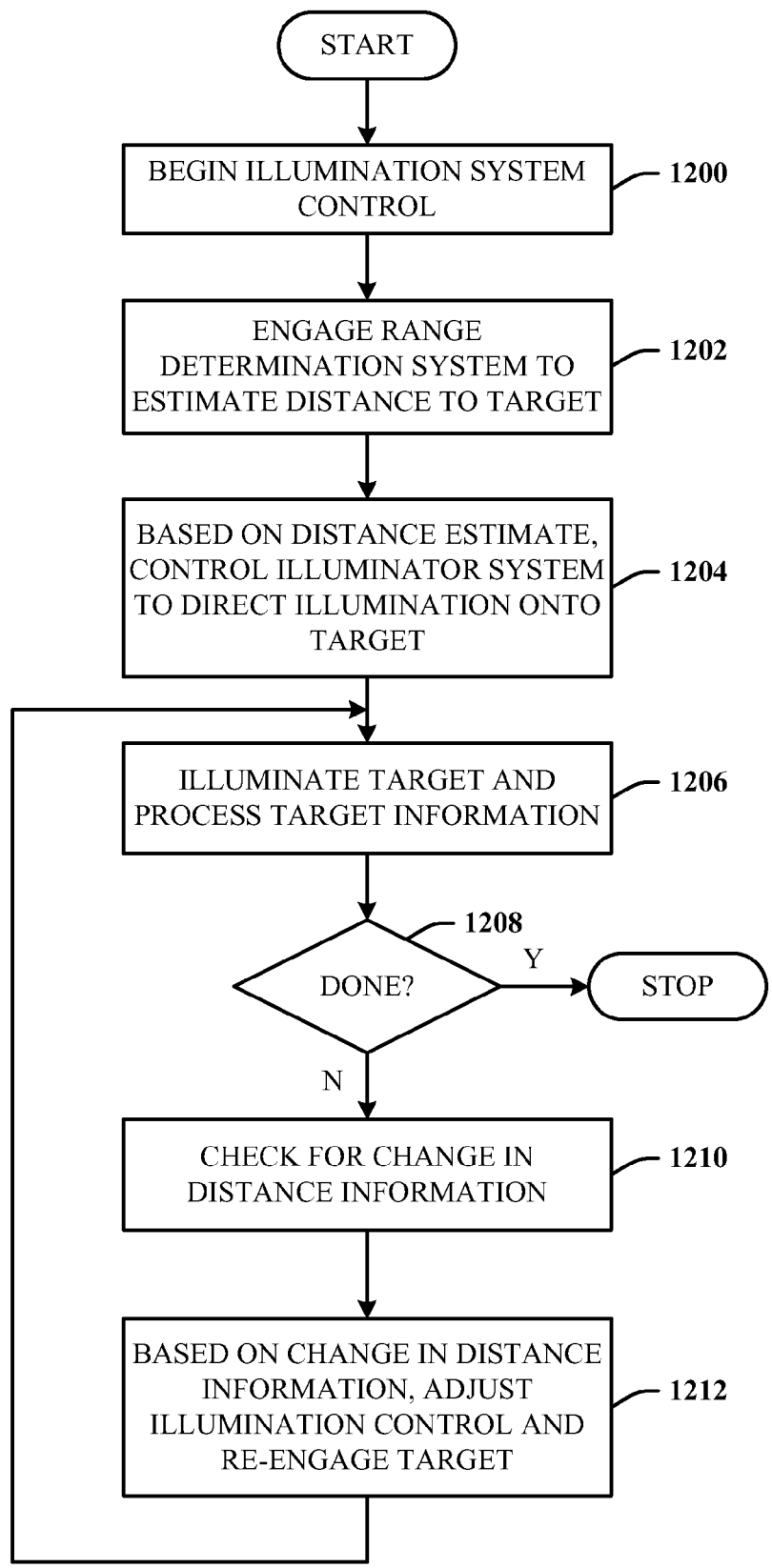
FIG. 12 illustrates a methodology of maintaining illumination control based on distance to target.

FIG. 12 illustrates a methodology of maintaining illumination control based on distance to target. At 1200, the system initiates an illumination control process. At 1202, the range determination system is enabled to estimate the distance to the target. At 1204, based on the distance estimate, the illumination system is controlled to direct illumination onto the target. At 1206, once the target is illuminated, target information is received back at the imager subsystem for analysis and processing for presence of the material of interest. At 1208, if no more target examination is required, flow stops. However, if further examination is warranted or desired, flow is to 1210, where the system can again check the distance to target for a change in distance information. At 1212, based on change in distance information, adjust the illumination servo control and re-engage target examination.

Figure 13:
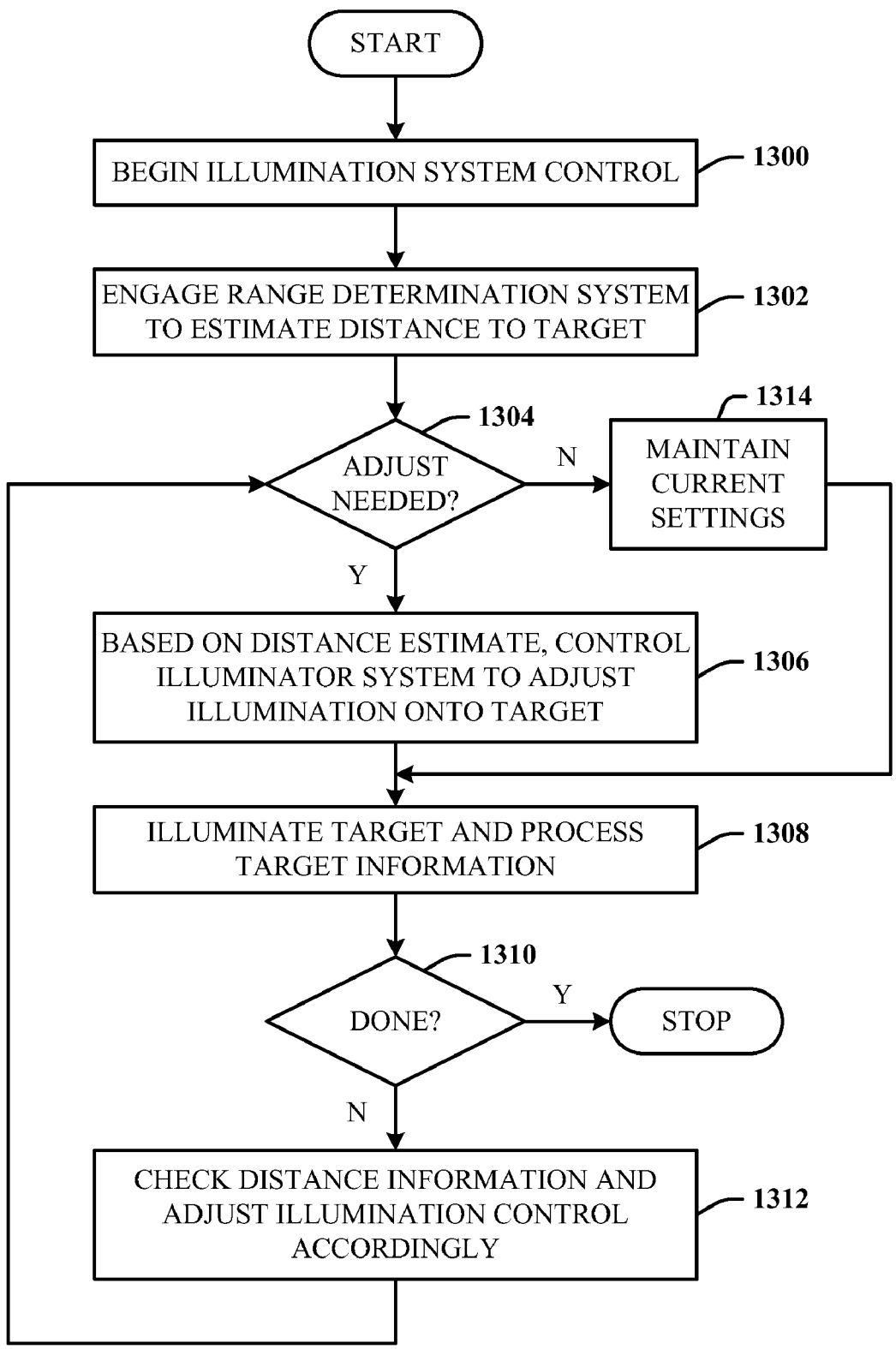
FIG. 13 illustrates a flow diagram of an alternative methodology of maintaining illumination control based on distance to target.

FIG. 13 illustrates a flow diagram of an alternative methodology of maintaining illumination control based on distance to target. At 1300, the system initiates an illumination control process. At 1302, the range determination system is enabled to estimate the distance to the target. At 1304, the system determines if the range to target value exceeds predetermined range criteria. Under such circumstances, the distance to target is sufficiently large such that illumination control is required, since the error in maintaining the illumination on the target is beyond acceptable limits. Accordingly, at 1306, the illuminator system is controlled to readjust the illumination onto the target. At 1308, the target is illuminated and examined for the material of interest. At 1310, the system checks to see if the examination process has completed. If not, flow is to 1312, to again check the distance information and adjust the illumination control accordingly. Flow is back to 1304 to check for a needed adjustment in, for example, beam dispersion or focus of the beam on target. If no adjustment is needed, flow is from 1304 to 1314, to maintain existing parameters or settings, and process target examination. Flow is then to 1308 where the target is illuminated and examined, and flow proceeds as described above.

It is to be understood that in many instances the distance to target is so small that illumination adjustment is not required. Such distances can be predetermined during system testing such that the distance information is readily available in lookup tables for rapid processing and assessment as to if further distance processing is required. In another implementation, these tables of distance information can serve as a default set of data which can be updated in the field according to the environment in which the system is deployed, or as needed.

Figure 14:
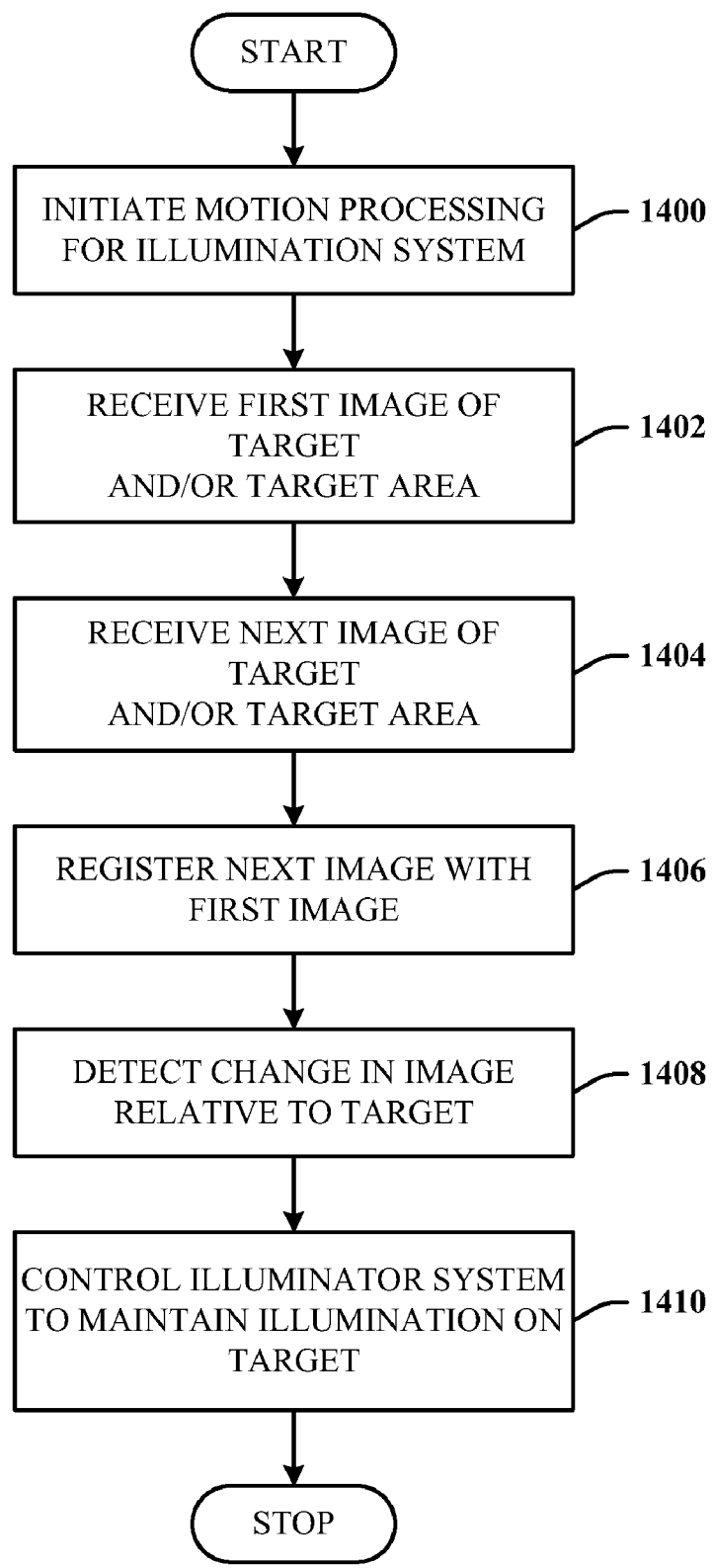
FIG. 14 illustrates a flow diagram of a methodology of image processing for motion analysis and illumination control in accordance with an innovative aspect.

FIG. 14 illustrates a flow diagram of a methodology of image (or frame) processing for motion analysis and illumination control in accordance with an innovative aspect. At 1400, motion processing is initiated. At 1402, a first image is received of the target and/or target area. At 1404, a next image is received of the target and/or target area. At 1406, registration is performed between the two images (or frames) in preparation for image processing. At 1408, based on image processing, the change in image data can be utilized to determine a corresponding change in motion of the illumination system relative to the target. At 1410, the illumination system is controlled dynamically to compensate for the change motion.

Figure 15:
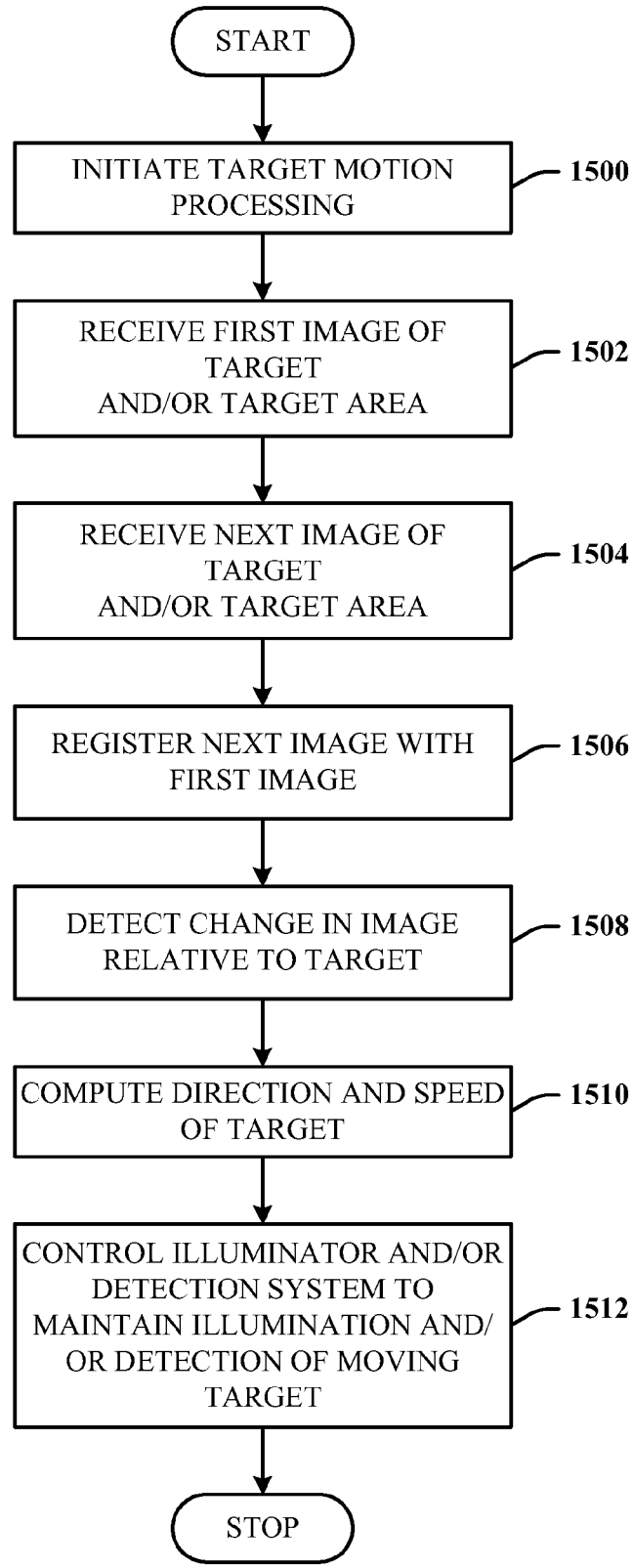
FIG. 15 illustrates a methodology of tracking a moving target and adjusting illumination control accordingly.

FIG. 15 illustrates a methodology of tracking a moving target and adjusting illumination control accordingly. At 1500, target motion processing is initiated. This can be a program that only executes when needed to reduce overhead processing in the system. At 1502, a first image is captured of the target and/or target area. At 1504, a next image is captured of the target and/or target area. At 1506, image registration is performed between the two images (or frames) in preparation for image processing. At 1508, based on image processing, the change in image data can be utilized to determine a corresponding change in motion of the illumination system relative to the target. At 1510, based on imaging processing, the heading and speed of the target can be computed relative to the illumination system. At 1512, the illumination and/or detection system is controlled dynamically to compensate for the change in speed and heading of the target. This process can be employed whether the illumination and/or detection system are in motion or not.

Figure 16:
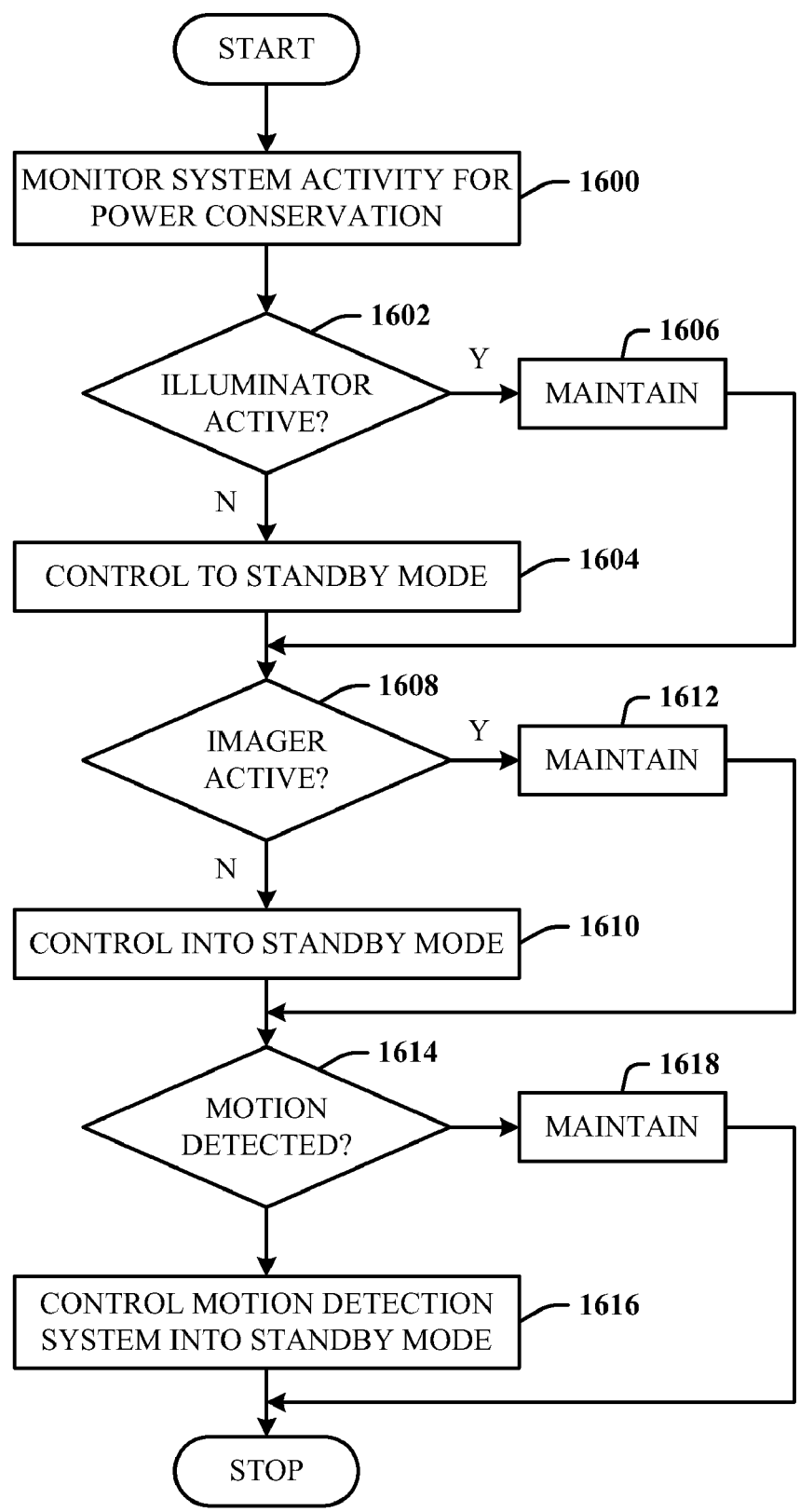
FIG. 16 illustrates a methodology of controlling power conservation of one or more illumination and detection subsystems.

FIG. 16 illustrates a methodology of controlling power conservation of one or more illumination and detection subsystems. At 1600, system activity of subsystems is monitored. At 1602, the system checks if the illuminator subsystem is active. If not, at 1604, the illuminator subsystem can be controlled into a standby mode to conserve system power. If so, at 1606, maintain operating power to this subsystem and flow to 1608 to check for activity in the imager subsystem. At 1608, the system checks if the imager subsystem is active. If not, at 1610, the imager subsystem can be controlled into a standby mode to conserve system power. If so, at 1612, maintain operating power to this subsystem and flow to 1614 to check for activity in the motion subsystem. At 1614, the system checks if the motion subsystem is active. If not, at 1616, the motion subsystem can be controlled into a standby mode to conserve system power. If so, at 1618, maintain operating power to this subsystem. Of course, this power conservation process can also apply to many other subsystems as desired. For example, the range finder subsystem can be controlled in a similar manner to conserve power.

Figure 17:
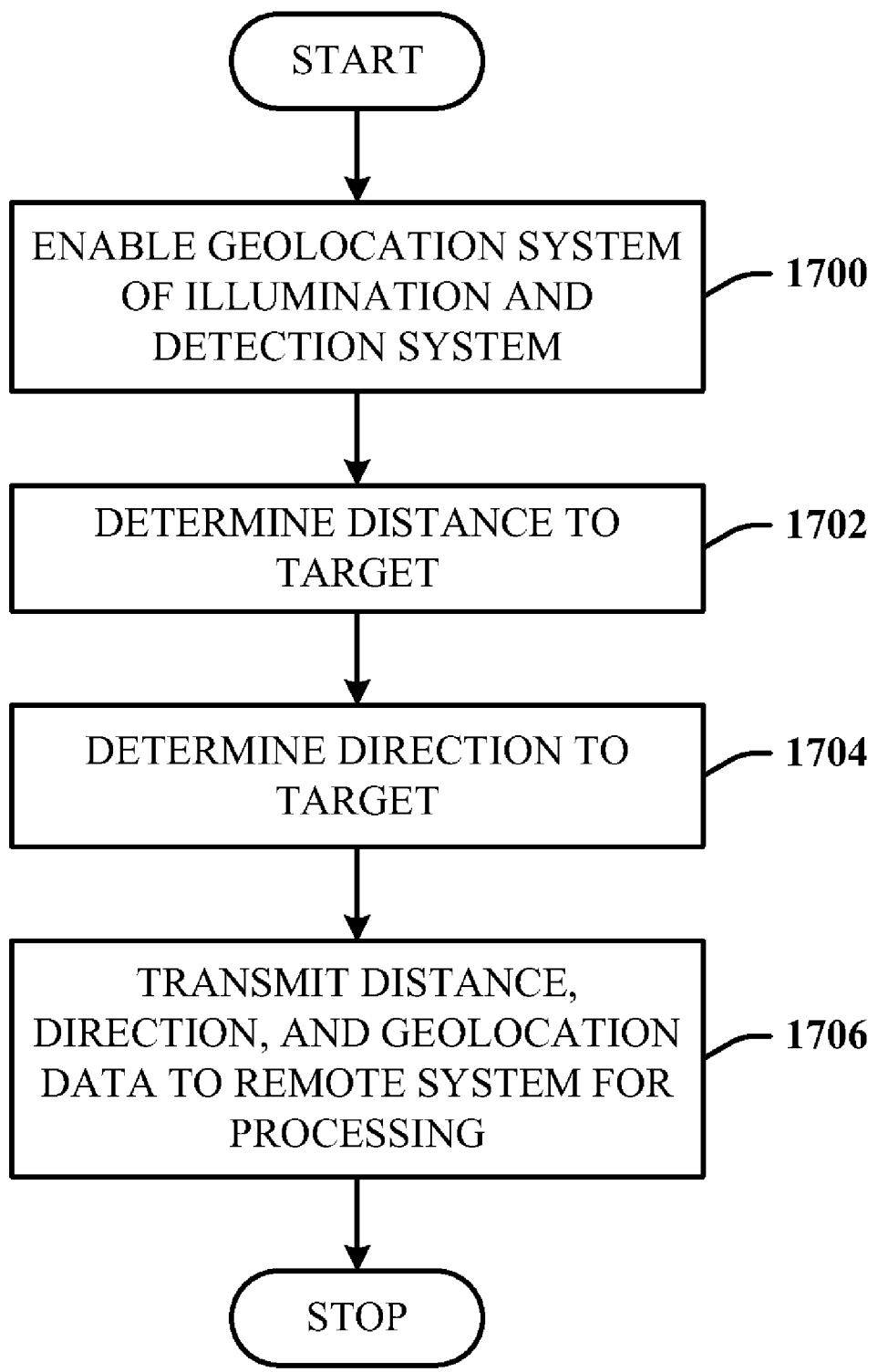
FIG. 17 illustrates a flow diagram of a methodology of employing and processing geolocation information in accordance with an innovative aspect.

FIG. 17 illustrates a flow diagram of a methodology of employing and processing geolocation information in accordance with an innovative aspect. At 1700, a geolocation subsystem of the illumination and detection system is enabled for operation, and receives coordinate information (e.g., lat/long data) that indicates the approximate geographic location of the geolocation receiver. At 1702, the range finder subsystem determines the range to target data. At 1704, the system determines the direction to target. This can be accomplished by known triangulation techniques, or simply approximating and entering such information into the system. At 1706, the distance data, direction data, and geolocation data can be transmitted to a remote location for further processing. Accordingly, such data can be utilized to define an approximate spatial relationship of the target and the illumination system, for example, on a geographic grid, for example.

Figure 18:
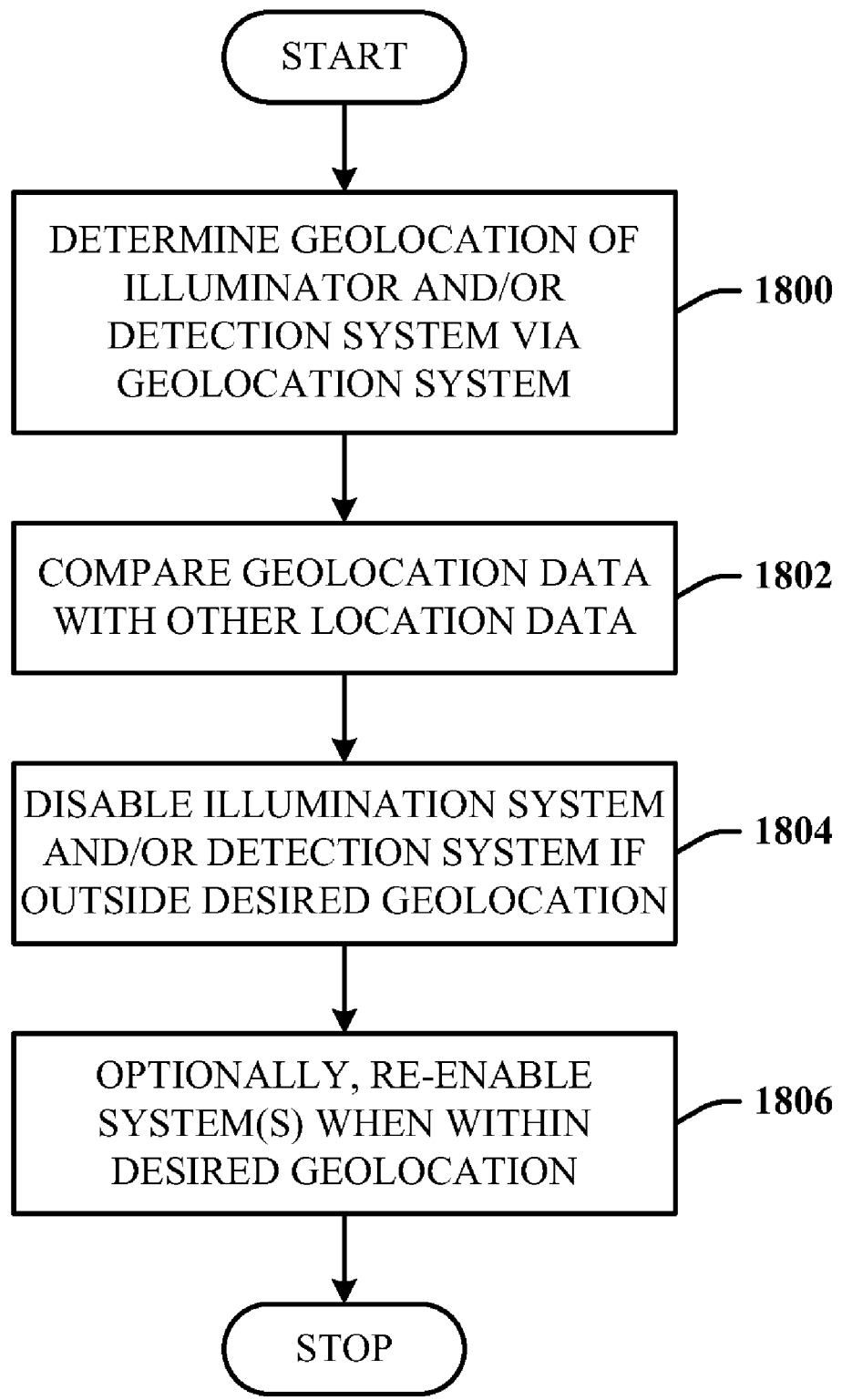
FIG. 18 illustrates a methodology of controlling operation of the illumination and/or detection systems based on geolocation data.

FIG. 18 illustrates a methodology of controlling operation of the illumination and/or detection systems based on geolocation data. For example, where such systems are deployed in a hostile environment, it may be desirable to disable (temporarily or permanently) operation of the systems from a remote location, similar to the LO-JACK technology used for tracking automobiles. Accordingly, at 1800, the geolocation subsystem (e.g., GPS) receives satellite information that approximates the location of the receiver. At 1802, the location information can be compared with other location information to determine whether the system is at a location where the system should be disabled. At 1804, the remote location can send a signal the disables the system. At 1806, optionally, the system can be operationally re-enabled as desired. It is to be appreciated that the system can be configured for destructive disablement to prevent access to internal system information.

Figure 19:
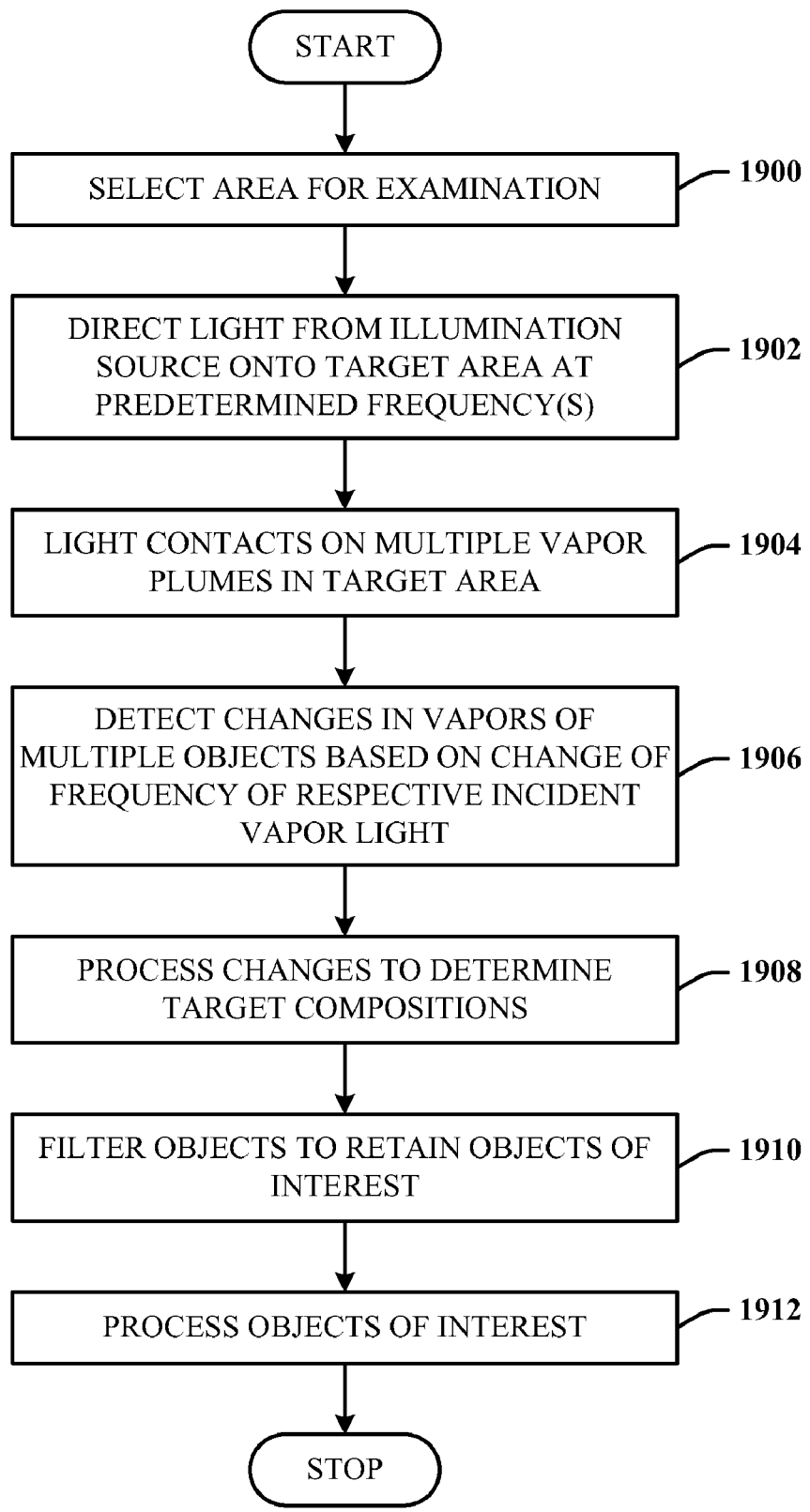
FIG. 19 illustrates a methodology of examining multiple targets, in accordance with an innovative aspect.

FIG. 19 illustrates a methodology of examining multiple targets, in accordance with an innovative aspect. At 1900, the target area is selected for examination, in which the materials of interest are anticipated to be. At 1902, light from the illumination source is directed toward the area in a dispersed fashion. Additionally, the illumination source is not limited to outputting a single wavelength if light, but can be multiple wavelengths (or a set of predetermined wavelengths) of a predetermined bandwidth in which a desired chemical property is (or properties are) expected to be detected. Moreover, the light beam can be expanded so as to be spread over a portion of the area or the whole area such that more than one instance of a material of interest can be energized for detection or more than one instance of different types of materials can be detected substantially simultaneously.

At 1904, light contacts multiple different vapors and/or particle compounds in the target area. At 1906, changes in the energized materials for the multiple targets are detected. For example, it is to be appreciated that the different wavelengths energize target materials differently such that the detected chemicals and/or compounds can be for a variety of different materials. Thus, multiple different types of targets can be detected substantially simultaneously in the area of interest. For example, it is possible that two target vapors are detected: one of a drug, and the other of an explosive. Moreover, these different target detections can be displayed to the user differently, using for example, a color yellow for explosives and a color blue for drugs. Other representative indicia can be employed for quick identification of the target chemical (e.g., differing audio signals).

At 1908, the detected information is processed to determine the target material compositions. At 1910, targets can be filtered to display only the desired object(s) in the area of interest. For example, if three different types of explosives are detected, it may be desired to only display one of the three targets. It is to be appreciated that filtering of information can be according to virtually any criteria the user desires. At 1912, only the objects of interest are retained or presented for human interaction or automatic processing. The filtering function is further aided by utilizing a single light frequency, or a select few of the light frequencies, thereby limiting the detectable interactions to a corresponding single type of chemical or the select few of detectable chemicals.

It is to be understood that the subject invention facilitates the immediate visual perception of the desired chemical indications, since the presence of the change can be visually perceived by the user immediately. For example, as the user looks through a scope or viewer at the target area, and the light beam impacts the chemical vapor, the viewer can process the detected change as brightness, or a change in color of the viewer window or display. Accordingly, the user knows immediately if a target chemical has been detected in the target area or on object by the unit.

It is within contemplation of the subject innovation that the systems and methods described herein can be configured to accommodate spectroscopy as a means for change detection. For example, Raman spectroscopy, laser-induced breakdown spectroscopy, NIR (near infrared) spectroscopy, and optical absorption techniques are also within contemplation for detection systems in accordance with the subject invention.

Figure 20:
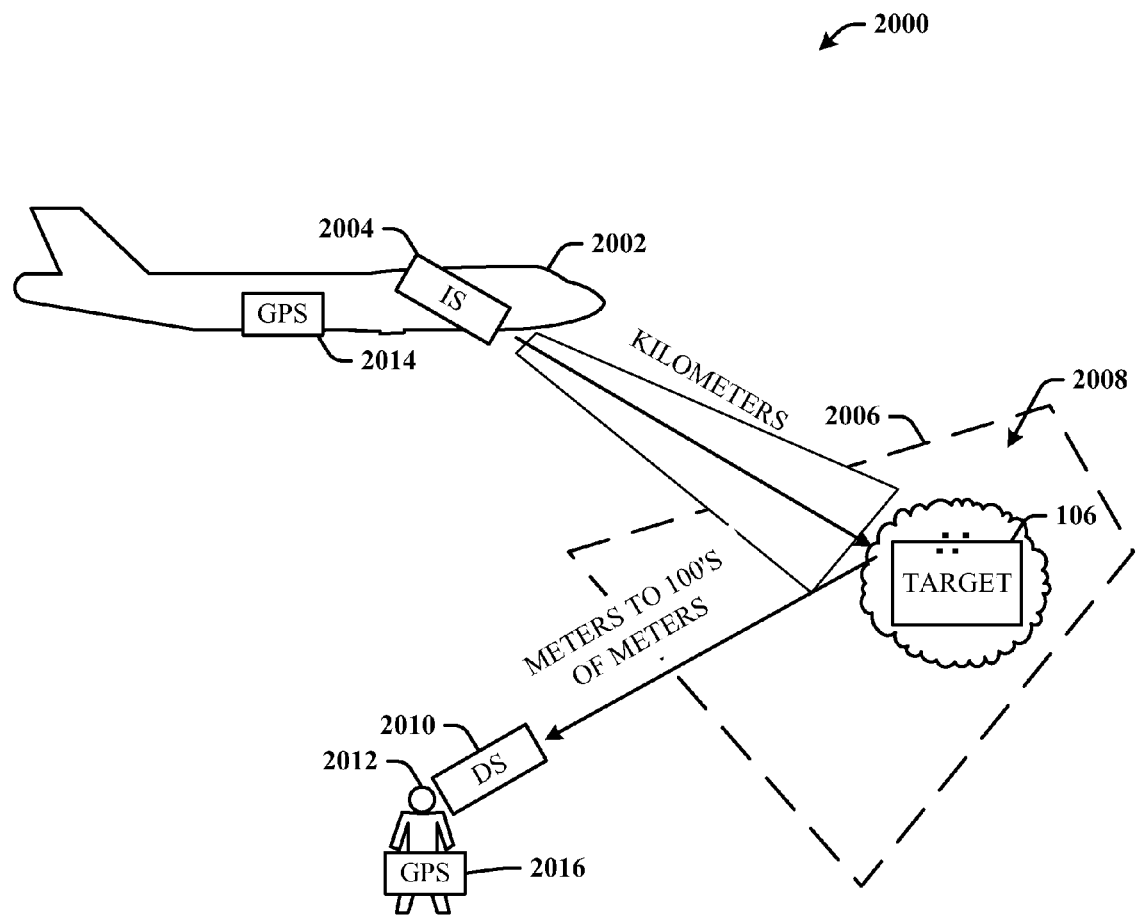
FIG. 20 illustrates an airborne system that employs target illumination and detection in accordance with the subject innovation.

FIG. 20 illustrates an airborne system 2000 that employs target illumination and detection in accordance with the subject innovation. Here, an airplane 2002 is used to transport an illumination system (IS) 2004 over a target area 2006 in which the target(s) 106 is anticipated to be. Once illuminated, the target material(s) 2008 change, which change is detected by a land-based detection system (DS) 2010 which can be, in some implementations, carried by a human 2012. For example, where the target 106 is being searched at night or under low-light conditions, the DS 2010 can be similar to the imaging and detection systems utilized in a night vision scope, such that a user observing the general target area 2006 would perceive the target 106 based upon the processed materials change data sensed by the detection system 2010. Again, either or both of the airplane 2002 or/and the human 2012 can include GPS systems 2014 or/and 2016, respectively, for locating the airplane 2002, the human 2012, and/or the target 106.

Note that depending on the type of light source, the distance for the source 2014 to the target 106 can be great distances. For example, the airplane (or any flying vehicle, e.g., a pilotless drone or helicopter) can be many kilometers (e.g., 15 km) from the target 106. The DS 2010 can be much closer, for example, meters to hundreds of meters from the target 106 in order to detect and perceive the materials change at the target 106.

It is within contemplation of the subject invention that in another implementation both the IS 2004 and the DS 2010 can be deployed from the aircraft 2002. Additionally, the disclosed architecture is not limited to aircraft applications, but can also be employed in combination with ships, trucks, and/or other types of moving vehicles or craft.

The IS 2004 can also be mounted on a fixed structure such that any object passing in a detection or scanning area can be illuminated, detected, and processed accordingly. For example, luggage passing through the scanning area can be quickly illuminated and processed for a potentially hazardous, illegal, and/or dangerous material. Another application is for shipping ports where residue can be quickly exposed under illumination and processed accordingly. Virtually any object or area can be scanned for the desired change in chemicals and/or compounds, for example, in accordance with the subject invention.

Figure 21:
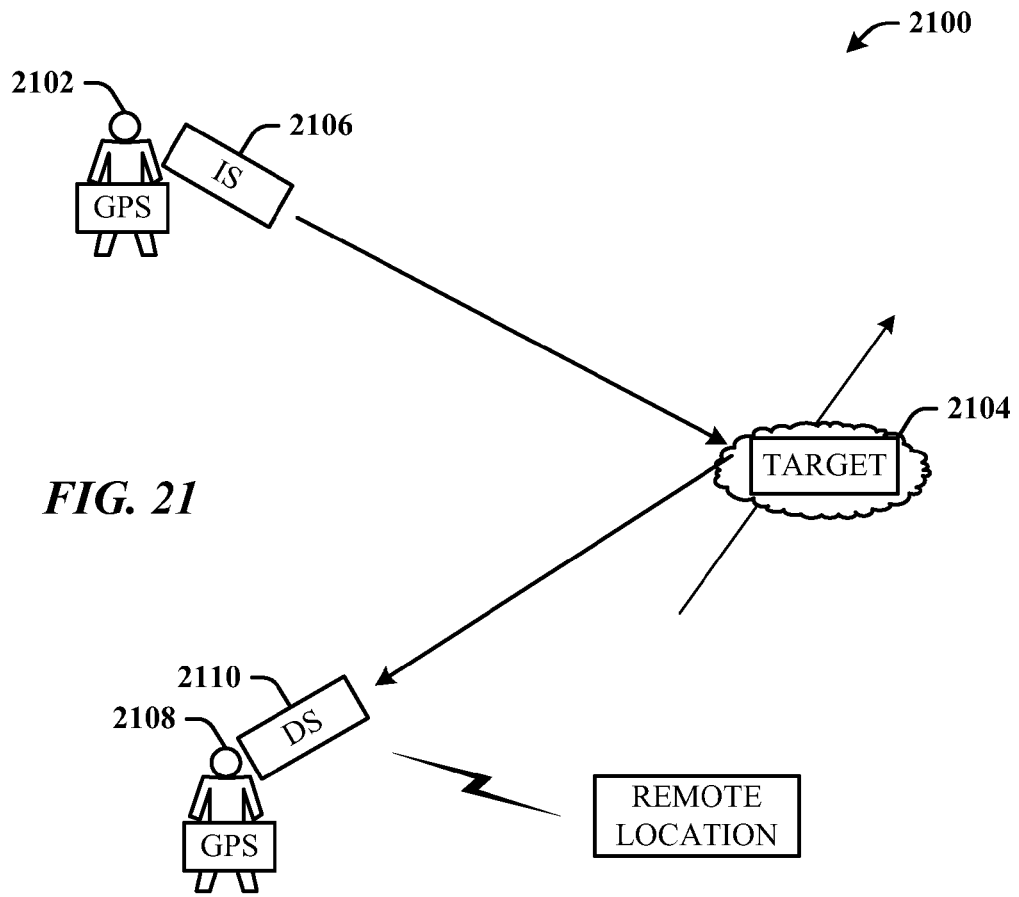
FIG. 21 illustrates a land-based two-user system (handheld or otherwise) that facilitates target illumination and detection in accordance with the subject invention.

FIG. 21 illustrates a land-based two-user system 2100 (handheld or otherwise) that facilitates target illumination and detection in accordance with the subject invention. A first user 2102 illuminates a mobile target 2104 with an IS 2106, which target 2104 "lights up" when the desired associated chemical property is detected by a second user 2108 who employs a DS 2110 pointed in the general area of the target 2104. Either or both of the first or/and second users (2102 and 2108) can further employ GPS systems for geolocation tracking, as described supra.

Figure 22:
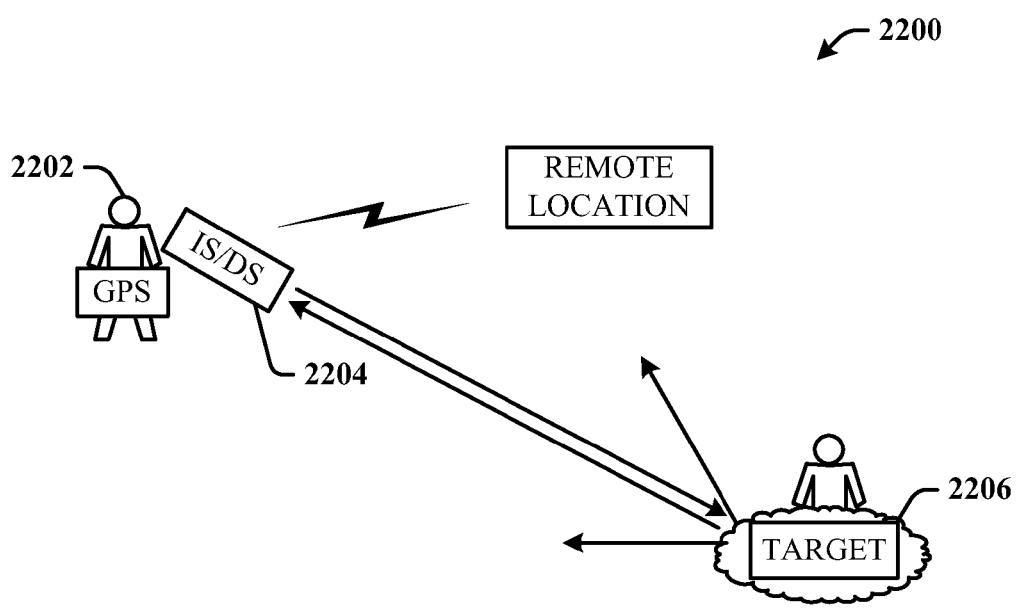
FIG. 22 illustrates a land-based single-user handheld system that facilitates target illumination and detection in accordance with the subject invention.

FIG. 22 illustrates a land-based single-user handheld system 2200 that facilitates target illumination and detection in accordance with the subject invention. A user 2202 utilizes a combined illumination/detection system 2204 (denoted IS/DS) which both illuminates a target 2206 and detects the materials change associated therewith, which target 2206 "lights up" when the desired chemical property is detected by system 2204 at the desired light wavelength. The user 2202 can also utilize a GPS system 2208 to receive and process geolocation coordinates information.

In both the system 2100 of FIG. 21 and the system 2200 of FIG. 22, data that is sensed can be stored locally for later transmission to a remote location. Alternatively, the DS 2110 of FIG. 21 and the IS/DS system 2204 can store and transmit the received materials change data in realtime, and any other associated signals and data wirelessly to a remote location.

Figure 23:
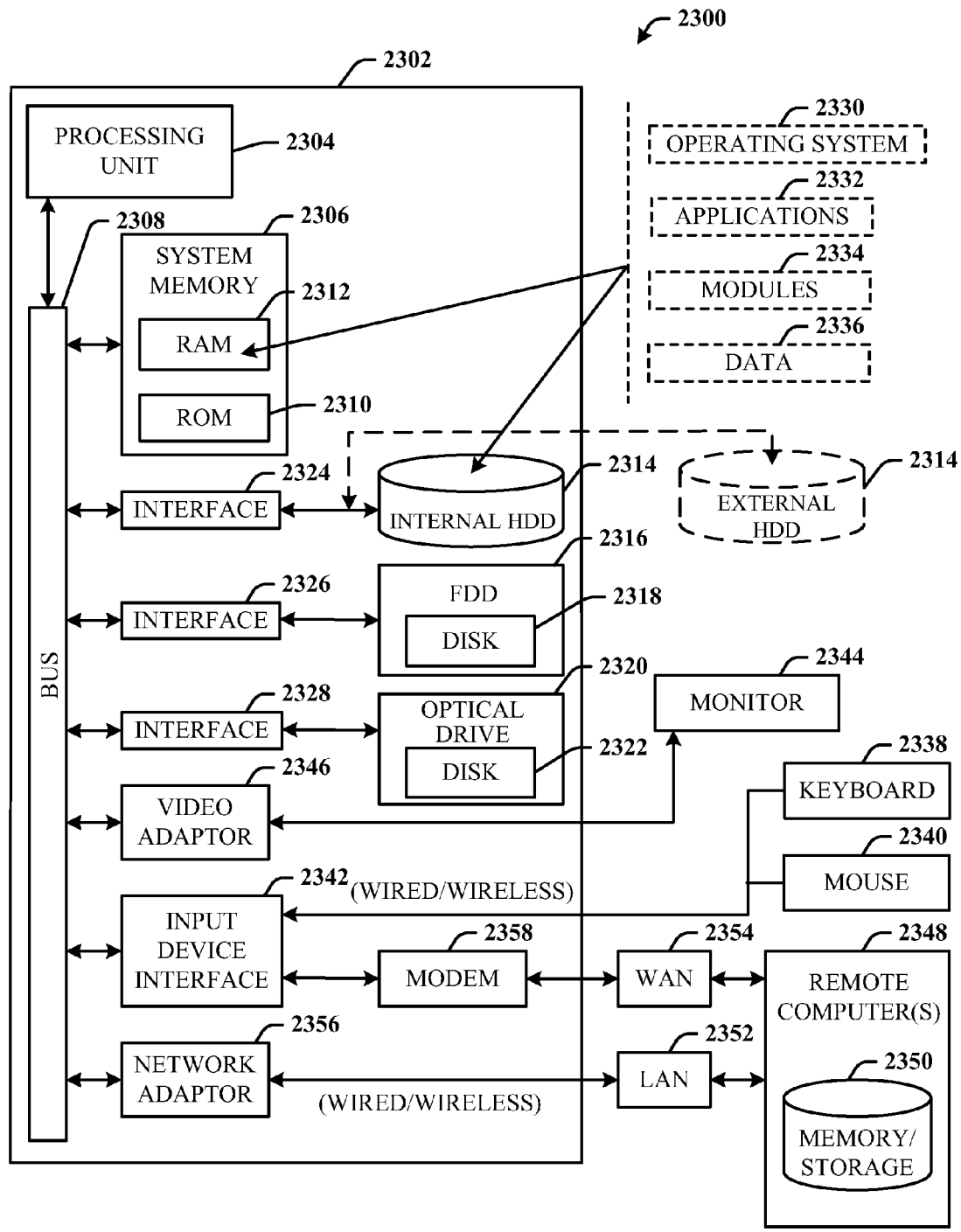
FIG. 23 illustrates a block diagram of a computer operable to execute the disclosed illumination and detection architecture.

Referring now to FIG. 23, there is illustrated a block diagram of an exemplary computer operable to execute the sensor data and/or the video processing capabilities of the disclosed architecture. In order to provide additional context for various aspects of the subject invention, FIG. 23 and the following discussion are intended to provide a brief, general description of a suitable computing environment 2300 in which the various aspects of the invention can be implemented. While the invention has been described above in the general context of computer-executable instructions that may run on one or more computers, those skilled in the art will recognize that the invention also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the invention may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer readable media can comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 23, the exemplary computing environment 2300 for implementing various aspects of the invention includes a computer 2302, the computer 2302 including a processing unit 2304, a system memory 2306 and a system bus 2308. The system bus 2308 couples system components including, but not limited to, the system memory 2306 to the processing unit 2304. The processing unit 2304 can be any of various commercially available processors. Dual microprocessors and other multi-processor architectures may also be employed as the processing unit 2304.

The system bus 2308 can be any of several types of bus structure that may further interconnect to a memory bus (with or without a memory controller), a peripheral bus, and a local bus using any of a variety of commercially available bus architectures. The system memory 2306 includes read only memory (ROM) 2310 and random access memory (RAM) 2312. A basic input/output system (BIOS) is stored in a non-volatile memory 2310 such as ROM, EPROM, EEPROM, which BIOS contains the basic routines that help to transfer information between elements within the computer 2302, such as during start-up. The RAM 2312 can also include a high-speed RAM such as static RAM for caching data.

The computer 2302 further includes an internal hard disk drive (HDD) 2314 (e.g., EIDE, SATA), which internal hard disk drive 2314 may also be configured for external use in a suitable chassis (not shown), a magnetic floppy disk drive (FDD) 2316, (e.g., to read from or write to a removable diskette 2318) and an optical disk drive 2320, (e.g., reading a CD-ROM disk 2322 or, to read from or write to other high capacity optical media such as the DVD). The hard disk drive 2314, magnetic disk drive 2316 and optical disk drive 2320 can be connected to the system bus 2308 by a hard disk drive interface 2324, a magnetic disk drive interface 2326 and an optical drive interface 2328, respectively. The interface 2324 for external drive implementations includes at least one or both of Universal Serial Bus (USB) and IEEE 1394 interface technologies. Other external drive connection technologies are within contemplation of the subject invention.

The drives and their associated computer-readable media provide nonvolatile storage of data, data structures, computer-executable instructions, and so forth. For the computer 2302, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules can be stored in the drives and RAM 2312, including an operating system 2330, one or more application programs 2332, other program modules 2334 and program data 2336. All or portions of the operating system, applications, modules, and/or data can also be cached in the RAM 2312. It is appreciated that the invention can be implemented with various commercially available operating systems or combinations of operating systems.

A user can enter commands and information into the computer 2302 through one or more wired/wireless input devices, e.g., a keyboard 2338 and a pointing device, such as a mouse 2340. Other input devices (not shown) may include a microphone, an IR remote control, a joystick, a game pad, a stylus pen, touch screen, or the like. These and other input devices are often connected to the processing unit 2304 through an input device interface 2342 that is coupled to the system bus 2308, but can be connected by other interfaces, such as a parallel port, an IEEE 1394 serial port, a game port, a USB port, an IR interface, etc.

A monitor 2344 or other type of display device is also connected to the system bus 2308 via an interface, such as a video adapter 2346. In addition to the monitor 2344, a computer typically includes other peripheral output devices (not shown), such as speakers, printers, etc.

The computer 2302 may operate in a networked environment using logical connections via wired and/or wireless communications to one or more remote computers, such as a remote computer(s) 2348. The remote computer(s) 2348 can be a workstation, a server computer, a router, a personal computer, portable computer, microprocessor-based entertainment appliance, a peer device or other common network node, and typically includes many or all of the elements described relative to the computer 2302, although, for purposes of brevity, only a memory storage device 2350 is illustrated. The logical connections depicted include wired/wireless connectivity to a local area network (LAN) 2352 and/or larger networks, e.g., a wide area network (WAN) 2354. Such LAN and WAN networking environments are commonplace in offices, and companies, and facilitate enterprise-wide computer networks, such as intranets, all of which may connect to a global communication network, e.g., the Internet.

When used in a LAN networking environment, the computer 2302 is connected to the local network 2352 through a wired and/or wireless communication network interface or adapter 2356. The adaptor 2356 may facilitate wired or wireless communication to the LAN 2352, which may also include a wireless access point disposed thereon for communicating with the wireless adaptor 2356.

When used in a WAN networking environment, the computer 2302 can include a modem 2358, or is connected to a communications server on the WAN 2354, or has other means for establishing communications over the WAN 2354, such as by way of the Internet. The modem 2358, which can be internal or external and a wired or wireless device, is connected to the system bus 2308 via the serial port interface 2342. In a networked environment, program modules depicted relative to the computer 2302, or portions thereof, can be stored in the remote memory/storage device 2350. It will be appreciated that the network connections shown are exemplary and other means of establishing a communications link between the computers can be used.

The computer 2302 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the invention. It is, of course, not possible to describe every conceivable combination of components or methodologies for purposes of describing the subject invention, but one of ordinary skill in the art may recognize that many further combinations and permutations of the invention are possible. Accordingly, the invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A portable handheld system, comprising:
an illumination component as part of an integral unit that directs electromagnetic radiation of a predetermined wavelength at a target associated with a material of interest, and which electromagnetic radiation causes a change in the electromagnetic radiation wavelength to occur when in contact with the material of interest;
a sensor component as part of the integral unit that senses the change in the electromagnetic radiation wavelength as change data;
an image processing component as part of the integral unit that receives the change data and creates images of the change data for analysis;
a change detection component as part of the integral unit that receives the images, analyzes the images to determine a type of the material of interest, and outputs the type as type information; and
a presentation component as part of the integral unit that displays the type information for visual perception by a user.

2. The system of claim 1, wherein the illumination component includes a laser unit that emits a beam of electromagnetic radiation of a predetermined wavelength at the target, and which electromagnetic radiation causes the change in the electromagnetic radiation wavelength to occur when in contact with the material of interest.

3. The system of claim 1, further comprising a geolocation component as part of the integral unit that provides location information as to location of the unit.

4. The system of claim 1, wherein the material of interest is associated with at least one of an atmospherically suspended or surface absorbed energetic nitrocompound, hazardous material, or drug.

5. The system of claim 1, wherein the integral unit is employed in combination a viewer through which a user views the target, and the presentation component displays a user-identifiable indication on the viewer that the material of interest is present or not present at the target.

6. The system of claim 1, wherein the illumination component illuminates the target with a range of electromagnetic radiation wavelengths to determine presence of multiple different types of materials of interest.

7. The system of claim 1, wherein the components of the integral unit operate to ultimately display the type information under low light and nighttime conditions.

8. The system of claim 1, wherein the illumination component disperses the electromagnetic radiation of a single wavelength over an area that includes the target to detect the material of interest in the area or a range of electromagnetic radiation having different wavelengths over the area that includes the target to detect correspondingly different materials of interest in the area.

9. The system of claim 1, wherein the integral unit is temporarily or destructively disabled, locally or from a remote location.

10. A portable handheld system, comprising:
an illumination component as part of an integral unit that directs electromagnetic radiation of a predetermined wavelength at a target associated with a material of interest, and which electromagnetic radiation causes a change in the electromagnetic radiation wavelength to occur when in contact with the material of interest;
a sensor component as part of the integral unit that senses the change in the electromagnetic radiation wavelength as change data;

an image processing component as part of the integral unit that receives the change data and creates images of the change data for analysis;

a change detection component as part of the integral unit that receives the images, analyzes the images to determine a type of the material of interest, and outputs the type as type information;

a range finder component as part of the integral unit that computes distance to the target;

a viewer through which a user views the target; and a presentation component as part of the integral unit that displays the type information for visual perception by a user via the viewer and a user-identifiable indication on the viewer that the material of interest is present or not present at the target.

11. The system of claim 10, further comprising a geolocation component as part of the integral unit that provides location information as to location of the integral unit.

12. The system of claim 10, wherein the material of interest is associated with at least one of an atmospherically suspended or surface absorbed energetic nitrocompound, hazardous material, or drug.

13. The system of claim 10, wherein the components of the integral unit operate to ultimately display the type information under low light and nighttime conditions.

14. The system of claim 10, wherein the illumination component disperses the electromagnetic radiation of a single wavelength over an area that includes the target to detect the material of interest in the area or a range of electromagnetic radiation having different wavelengths over the area that includes the target to detect correspondingly different materials of interest in the area.

15. A computer-implemented method of determining a material of interest associated with a target, comprising:
illuminating a target from a handheld unit using electromagnetic radiation of a predetermined wavelength to identify a material of interest;
sensing a changed wavelength of the electromagnetic radiation as change data when the electromagnetic radiation impinges on the material of interest creating an image of the change data;
analyzing the change data via the image;
detecting a type of the material of interest based on analysis of the change data;
outputting the type as type information to a display; and
presenting the type information for viewing.

16. The method of claim 15, further comprising viewing the target through a viewer while illuminating the target.

17. The method of claim 16, further comprising presenting the type information on the viewer when viewing the target.

18. The method of claim 16, further comprising:
computing distance to the target for presentation on the viewer; and
adjusting illumination on the target based on the distance.

19. The method of claim 15, further comprising:
illuminating the target using electromagnetic radiation of additional predetermined wavelengths to identify additional materials of interest; and
presenting the type information of sensed additional materials of interest on a viewer through which the target is being viewed.

20. The method of claim 15, further comprising tracking location of the unit via a geolocation technology.

* * * * *